United States Patent
Kuboyama et al.

(10) Patent No.: US 9,839,616 B2
(45) Date of Patent: Dec. 12, 2017

(54) LIPID NANO PARTICLES COMPRISING CATIONIC LIPID FOR DRUG DELIVERY SYSTEM

(71) Applicant: Kyowa Hakko Kirin Co., Ltd., Tokyo (JP)

(72) Inventors: Takeshi Kuboyama, Tokyo (JP); Tomohiro Era, Tokyo (JP); Tomoyuki Naoi, Tokyo (JP)

(73) Assignee: KYOWA HAKKO KIRIN CO., LTD., Tokyo (JP)

(*) Notice: Subject to any disclaimer, the term of this patent is extended or adjusted under 35 U.S.C. 154(b) by 0 days.

(21) Appl. No.: 13/711,922

(22) Filed: Dec. 12, 2012

(65) Prior Publication Data

US 2014/0039032 A1 Feb. 6, 2014

Related U.S. Application Data

(60) Provisional application No. 61/670,854, filed on Jul. 12, 2012, provisional application No. 61/569,400, filed on Dec. 12, 2011.

(51) Int. Cl.
| | | |
|---|---|---|
| A61K 48/00 | (2006.01) |
| A61K 9/127 | (2006.01) |
| C12N 15/88 | (2006.01) |
| A61K 9/51 | (2006.01) |
| A61K 47/18 | (2017.01) |
| C07C 211/21 | (2006.01) |
| A61K 31/7088 | (2006.01) |
| A61K 9/00 | (2006.01) |
| A61K 31/712 | (2006.01) |
| C12N 15/113 | (2010.01) |

(52) U.S. Cl.
CPC .......... *A61K 9/5123* (2013.01); *A61K 9/0019* (2013.01); *A61K 31/7088* (2013.01); *A61K 31/712* (2013.01); *A61K 47/18* (2013.01); *C07C 211/21* (2013.01); *C12N 15/113* (2013.01); *C12N 15/88* (2013.01); *C12N 2310/14* (2013.01); *C12N 2310/321* (2013.01)

(58) Field of Classification Search
CPC .... A61K 31/7088; A61K 47/18; A61K 48/00; A61K 9/127; C07C 211/21
USPC ..................... 435/375, 458; 514/44; 424/450
See application file for complete search history.

(56) References Cited

U.S. PATENT DOCUMENTS

| | | | |
|---|---|---|---|
| 5,049,386 A | 9/1991 | Eppstein et al. | |
| 5,753,613 A | 5/1998 | Ansell et al. | |
| 5,785,992 A | 7/1998 | Ansell et al. | |
| 5,929,026 A * | 7/1999 | Childs et al. | 510/520 |
| 6,034,137 A | 3/2000 | Belloni et al. | |
| 6,656,498 B1 | 12/2003 | Gao | |
| 2003/0049310 A1 | 3/2003 | Gao | |
| 2006/0008519 A1 | 1/2006 | Davidsen et al. | |
| 2006/0057194 A1 | 3/2006 | Gao | |
| 2006/0083780 A1 * | 4/2006 | Heyes et al. | 424/450 |
| 2010/0226975 A1 | 9/2010 | Davidsen et al. | |

FOREIGN PATENT DOCUMENTS

| | | |
|---|---|---|
| JP | 10-152461 | 6/1998 |
| JP | 10-509418 | 9/1998 |
| JP | 2008-505131 | 2/2008 |
| WO | 91/16024 | 10/1991 |
| WO | 97/19675 | 6/1997 |
| WO | 98/51278 | 11/1998 |
| WO | 00/30444 | 6/2000 |
| WO | 2005/121348 | 12/2005 |
| WO | 2009/086558 | 7/2009 |
| WO | 2011/136368 | 11/2011 |

* cited by examiner

Primary Examiner — Janet Epps-Smith
(74) Attorney, Agent, or Firm — Wenderoth, Lind & Ponack, L.L.P.

(57) ABSTRACT

The present invention provides a lipid nano-particles, which allow nucleic acids to be easily introduced into cells, comprising a cationic lipid represented by formula (I)
(wherein: $R^1$ and $R^2$ are, the same or different, alkenyl, etc, and
$X^3$ is absent or is alkyl, etc,
$X^1$ and $X^2$ are hydrogen atoms, or are combined together to form a single bond or alkylene, and
$Y^1$ is absent or anion,
$L^1$ is a single bond, etc,
$R^3$ is alkyl, etc), and the like.

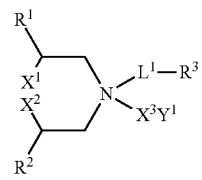

(I)

18 Claims, 4 Drawing Sheets

LIPID NANO PARTICLES COMPRISING CATIONIC LIPID FOR DRUG DELIVERY SYSTEM

FIELD OF THE INVENTION

The present invention relates to, for example, lipid nano particles comprising cationic lipid for drug delivery (drug delivery system) which enables introducing nucleic acids into cells, and the like.

BACKGROUND ART

Cationic lipids are amphiphilic molecules that generally contain a lipophilic region containing one or more hydrocarbon groups, and a hydrophilic region containing at least one positively charged polar head group. Cationic lipids are useful, because cationic lipids facilitate entry of macromolecules such as nucleic acids into the cytoplasm through the cell plasma membrane by forming a positively charged (total charge) complex with macromolecules such as nucleic acids. This process, performed in vitro and in vivo, is known as transfection.

Typically, cationic lipids are used either alone, or in combination with neutral lipids such as phospholipids. A combination of cationic lipids and neutral lipids is known to be useful, because it can easily form a vesicle that contains an aligned lipid bilayer. Vesicles and liposomes formed by cationic lipids either alone or in combination with neutral lipids have many positive charges on the surface, and, with these charges, can form a complex with polynucleotides or other anionic molecules such as negatively charged proteins. The remaining total cationic charge on the surface of a polynucleotide/cationic lipid/neutral lipid complex can cause strong interaction with the cell membrane, mainly with the negative charge on the surface of the cell membrane.

To date, many different cationic lipids have been synthesized for transfection, and are commercially available. Such cationic lipids include, for example, Lipofectin, Lipofectin ACE, Lipofect AMINE, Transfeactam, DOTAP, etc.

The N-[1-(2,3-dioleyloxy)propyl]-N,N,N-trimethylammonium chloride (DOTMA), etc disclosed in Patent Document 1 are one of the cationic lipids developed in the early. DOTMA etc. are characterized by the propanaminium group having quaternary nitrogen providing a cationic part to the molecule, and a pair of higher hydrocarbons attached to the propyl backbone of the molecule by an ether bond. The quaternary nitrogen is trisubstituted with relatively short alkyl chains such as methyl groups. As structurally similar cationic lipid, N-(2,3-di-(9-(Z)-octadecenoyloxy))-prop-1-yl-N,N,N-trimethylammonium chloride (DOTAP) contains acyl groups, instead of the ether-bonded alkyl groups.

For example, the N-[1-(2,3-dioleyloxypropyl)]-N,N-dimethyl-N-hydroxyethylammonium bromide (DORIE), 2,3-dioleyloxy-N-[2-(spermine carboxamido)ethyl]-N,N-dimethyl-1-propanaminium trifluoroacetate (DOSPA), etc disclosed in Patent Documents 2 and 3 are characterized by the propanaminium group having quaternary nitrogen providing a cationic part to the molecule, and a pair of higher hydrocarbons attached to the propyl backbone of the molecule by an ether bond, the propanaminium group. The quaternary nitrogen is characterized by being trisubstituted with relatively short alkyl chains such as methyl groups, and with hydroxyalkyl.

Patent Document 4 discloses, for example, 1,2-dilinoleyloxy-N,N-dimethylaminopropane (DLinDMA) etc. DLinDMA etc. are characterized in that for the purpose of developing more flexible cationic lipids, thereby increasing the membrane fluidity of a liposome or the like, the higher alkyl groups of DOTAP and DOTMA that are structurally analogous cationic lipids thereto are replaced by higher alkyl groups containing at least two sites of unsaturation. In addition, Patent Document 5 discloses, for example, 2,2-dilinoleyl-4-dimethylaminomethyl-[1,3]-dioxolane (DLin-K-DMA) etc.

Patent Document 6 discloses, for example, (3R,4R)-3,4-bis((Z)-hexadeca-9-enyloxy)-1-methylpyrrolidine (Compound 14), N-methyl-N,N-bis(2-((z)-octadeca-6-enyloxy)ethyl)amine (Compound 36), etc.

On the other hand, Patent Document 7 discloses cationic lipids such as N-methyl-N,N-dioleylamine etc. which are simple alkylamine type (or salts thereof).

CITATION LIST

Patent Documents

Patent Document 1: Japanese Published Unexamined Patent Application No. 161246/1986 (U.S. Pat. No. 5,049,386)
Patent Document 2: WO1991/16024
Patent Document 3: WO1997/019675
Patent Document 4: WO2005/121348
Patent Document 5: WO2009/086558
Patent Document 6: WO2011/136368
Patent Document 7: WO1998/051278

SUMMARY OF THE INVENTION

Problems to be Solved by the Invention

An object of the present invention is to provide lipid nano particles for drug delivery (drug delivery system) comprising cationic lipids that allows, for example, nucleic acids to be easily introduced into cells, and the like.

Means for Solving the Problems

The present invention relates to the following (1) to (24).
(1) Lipid nano particles for drug delivery comprising;
a cationic lipid represented by formula (I):

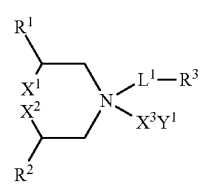

(wherein:
$R^1$ and $R^2$ are, the same or different, each linear or branched alkyl, alkenyl or alkynyl having 10 to 24 carbon atoms,
$X^1$ and $X^2$ are hydrogen atoms, or are combined together to form a single bond or alkylene,
$X^3$ is absent or is alkyl having 1 to 6 carbon atoms, or alkenyl having 3 to 6 carbon atoms,
when $X^3$ is absent,
$Y^1$ is absent, $L^1$ is a single bond, $R^3$ is hydrogen atom, alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, or $Y^1$ is absent, $L^1$ is —CO— or —CO—O—, $R^3$ is pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl, and when $X^3$ is alkyl having 1 to 6 carbon atoms or alkenyl having 3 to 6 carbon atoms, $Y^1$ is a pharmaceutically acceptable anion, $L^1$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl).

(2) The lipid nano particles for drug delivery as set forth above in (1), wherein $R^1$ and $R^2$ are dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl.

(3) The lipid nano particles for drug delivery as set forth above in (1), wherein $R^1$ and $R^2$ are tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl or (11Z,14Z)-icosa-11,14-dienyl.

(4) The lipid nano particles for drug delivery as set forth above in any one of (1) to (3), wherein $L^1$ is a single bond, $R^3$ is a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl.

(5) The lipid nano particles for drug delivery as set forth above in any one of (1) to (3), wherein $L^1$ is —CO— or —CO—O—, $R^3$ is pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl.

(6) The lipid nano particles for drug delivery as set forth above in any one of (1) to (5), wherein $X^1$ and $X^2$ are combined together to form a single bond or alkylene.

(7) The lipid nano particles for drug delivery as set forth above in any one of (1) to (5), wherein $X^1$ and $X^2$ are combined together to form a single bond or alkylene, and $R^3$ is a hydrogen atom, methyl or alkyl having a carbon number of from 1 to 6 or alkenyl having a carbon number of from 3 to 6, each substituted with 1 to 3 substituent(s), which is(are), the same or different, amino, hydroxy or carbamoyl.

(8) The lipid nano particles for drug delivery as set forth above in any one of (1) to (5), wherein $X^1$ and $X^2$ are hydrogen atoms, and $R^3$ is a hydrogen atom, methyl or alkyl having a carbon number of from 1 to 6 or alkenyl having a carbon number of from 3 to 6, each substituted with 1 to 3 substituent(s), which is(are), the same or different, amino, hydroxy or carbamoyl.

(9) The lipid nano particles for drug delivery as set forth above in any one of (1) to (8), wherein $X^3$ is absent.

(10) The lipid nano particles as set forth above in any one of (1) to (9), which comprise a nucleic acid as drug.

(11) The lipid nano particles as set forth above in (10), wherein the cationic lipid forms a complex together with the nucleic acid, or forms a complex between a combination of the cationic lipid with a neutral lipid and/or a polymer and the nucleic acid.

(12) The lipid nano particles for drug delivery as set forth above in (10), wherein the cationic lipid forms a complex together with the nucleic acid, or forms a complex between a combination of the cationic lipid with a neutral lipid and/or a polymer and the nucleic acid, and the composition comprises the complex and a lipid membrane for encapsulating the complex.

(13) The lipid nano particles for drug delivery as set forth above in any one of (10) to (12), wherein the nucleic acid is a nucleic acid having an activity of suppressing the expression of the target gene by utilizing RNA interference (RNAi).

(14) The lipid nano particles for drug delivery as set forth above in (13), wherein the target gene is a gene associated with tumor or inflammation.

(15) A method for introducing the nucleic acid into a cell by using the lipid nano particles for drug delivery of any one as set forth above in (10) to (14).

(16) The method as set forth above in (15), wherein the cell is a cell at a tumor or inflammation site of a mammal.

(17) The method as set forth above in (15) or (16), wherein the cell is a cell in the liver, lungs, kidneys or spleen of a mammal.

(18) The method as set forth above in (16) or (17), wherein the method of the introduction into a cell is a method of introduction into a cell by intravenous administration.

(19) A method for treating cancer or inflammatory disease, the method including administering the lipid nano particles for drug delivery of any one as set forth above in (1) to (14) to a mammal.

(20) The method as set forth above in (19), wherein the method of administration is intravenous administration.

(21) A medicament comprising the lipid nano particles for drug delivery of any one as set forth above in (1) to (14) and for treating disease.

(22) The medicament as set forth above in (21), which is for intravenous administration.
(23) A cancer or inflammatory disease therapeutic agent comprising the lipid nano particles for drug delivery of any one as set forth above in (1) to (14) and for treating cancer or inflammatory disease.
(24) The cancer or inflammatory disease therapeutic agent as set forth above in (23), which is for intravenous administration.

Effects of the Invention

The lipid nano particles for drug delivery (drug delivery system) of the present invention comprising, for example, a nucleic acid can be administered to mammals, etc and, for example, the like to easily introduce the nucleic acid into cells and the like.

MODES FOR CARRYING OUT THE INVENTION

Figure 1:
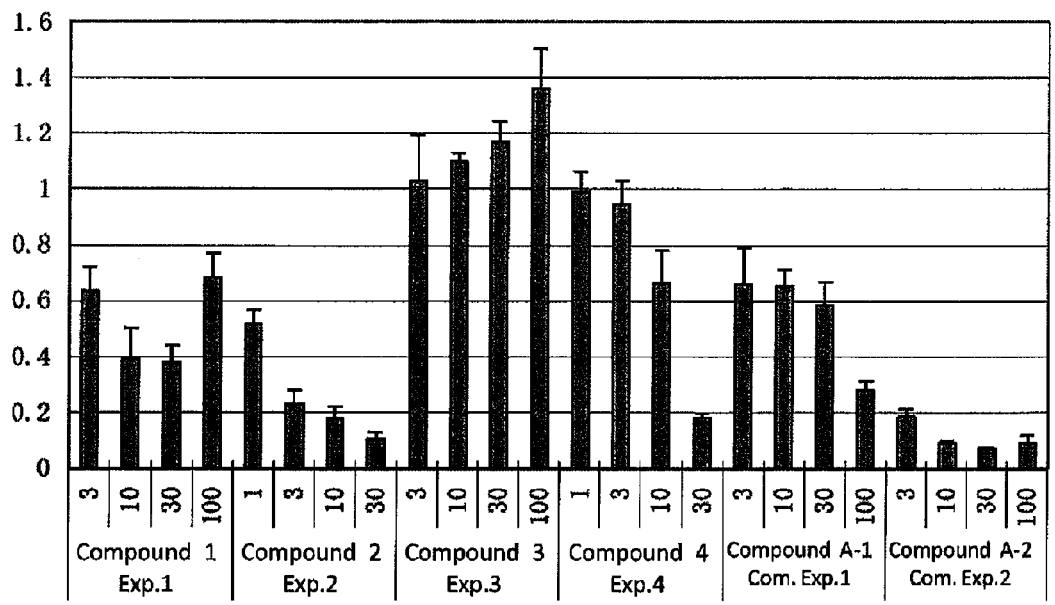
FIG. 1 shows the expression rate of target gene mRNA after the introduction of the preparations obtained in Examples 1 to 4 (preparations using compounds 1 to 4) and the preparations obtained in Comparative Examples 1 and 2 (preparations using compounds A-1 and A-2) into human liver cancer-derived cell line HepG2. The ordinate represents target gene mRNA expression rate relative to the negative control taken at 1; the abscissa represents nucleic acid concentration (nM), and the compound numbers of the cationic lipids used.

The cationic lipids contained in the lipid nano particles of the present invention are a compound represented by the following formula (I):

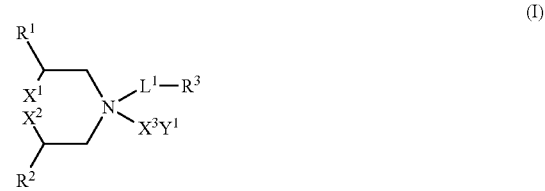

(I)

(wherein:
$R^1$ and $R^2$ are, the same or different, each linear or branched alkyl, alkenyl or alkynyl having 10 to 24 carbon atoms,
$X^1$ and $X^2$ are hydrogen atoms, or are combined together to form a single bond or alkylene,
$X^3$ is absent or is alkyl having 1 to 6 carbon atoms, or alkenyl having 3 to 6 carbon atoms,
when $X^3$ is absent,
$Y^1$ is absent, $L^1$ is a single bond, $R^3$ is hydrogen atom, alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, or
$Y^1$ is absent, $L^1$ is —CO— or —CO—O—, $R^3$ is pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl, and
when $X^3$ is alkyl having 1 to 6 carbon atoms or alkenyl having 3 to 6 carbon atoms,
$Y^1$ is a pharmaceutically acceptable anion, $L^1$ is a single bond, $R^3$ is alkyl having 1 to 6 carbon atoms, alkenyl having 3 to 6 carbon atoms, pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl).

The compound represented by the formula (I) will be hereinafter also referred to as "compound (I)". The same is also applicable to compounds designated with other numbers.

In the definition of each group of the formula (I), examples of the linear or branched alkyl having a carbon number of from 10 to 24 include decyl, undecyl, dodecyl, tridecyl, 6,10-dimethylundec-2-yl, tetradecyl, pentadecyl, hexadecyl, heptadecyl, octadecyl, 6,10,14-trimethylpentadecan-2-yl, nonadecyl, icosyl, henicosyl, docosyl, tricosyl, and tetracosyl.

The linear or branched alkenyl having a carbon number of from 10 to 24 may be linear or branched alkenyl having a carbon number of from 10 to 24 and having from 1 to 3 double bonds. Examples thereof include (Z)-dodec-7-enyl, (Z)-tetradec-7-enyl, (Z)-tetradec-9-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-6-enyl, (Z)-octadec-9-enyl, (E)-octadec-9-enyl, (9Z,12Z)-octadeca-9,12-dienyl, (Z)-octadec-11-enyl, (9Z,12Z,15Z)-octadeca-9,12,15-trienyl, (Z)-icos-11-enyl, and (11Z,14Z)-icosa-11,14-dienyl. Of these, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl, (11Z,14Z)-icosa-11,14-dienyl, and the like are preferable. Of these, (7Z,10Z)-hexadec-7,10-dienyl, (9Z,12Z)-octadec-9,12-dienyl, and the like are more preferable.

The linear or branched alkynyl having a carbon number of from 10 to 24 may be linear or branched alkynyl having a carbon number of from 10 to 24 and having from 1 to 3 triple bonds. Examples thereof include dec-9-ynyl, dodec-4-ynyl, dodec-11-ynyl, tetradec-5-ynyl, tetradec-6-ynyl, hexadec-7-ynyl, hexadeca-3,5-diynyl, hexadeca-5,7-diynyl, and octadec-9-ynyl.

Incidentally, in Compound (I), it is more preferable that $R^1$ and $R^2$ are the same, and are linear or branched alkyl, alkenyl or alkynyl having a carbon number of from 10 to 24. In addition, it is more preferable that each of $R^1$ and $R^2$ is linear or branched alkyl or alkenyl having a carbon number of from 10 to 24; and still more preferable that each of $R^1$ and $R^2$ is linear alkenyl having a carbon number of from 10 to 24.

Examples of the alkylene include methylene, ethylene, and propylene.

Examples of the alkyl having a carbon number of from 1 to 6 include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl, and cyclohexyl. Of these, methyl, ethyl, propyl, isopropyl, butyl, isobutyl, sec-butyl, tert-butyl, pentyl, isopentyl, sec-pentyl, tert-pentyl, neopentyl, hexyl, and the like are preferable, with methyl, ethyl, propyl, and the like being more preferable.

Examples of the alkenyl having a carbon number of from 3 to 6 include allyl, 1-propenyl, butenyl, pentenyl, and hexenyl. Of these, allyl and the like are preferable.

The alkyl moiety in the substituted alkyl having a carbon number of from 1 to 6 and the alkenyl moiety in the substituted alkenyl having a carbon number of from 3 to 6 are synonymous with the alkyl having a carbon number of from 1 to 6 and the alkenyl having a carbon number of from 3 to 6 as described above, respectively.

In Compound (I), examples of the pharmaceutically acceptable anion include inorganic ions such as a chloride ion, a bromide ion, a nitrate ion, a sulfate ion, and a phosphate ion; and organic acid ions such as an acetate ion, an oxalate ion, a maleate ion, a fumarate ion, a citrate ion, a benzoate ion, and a methanesulfonate ion.

In Compound (I), each of pyrrolidin-2-yl, pyrrolidin-3-yl, piperidin-2-yl, piperidin-3-yl, piperidin-4-yl, morpholin-2-yl, and morpholin-3-yl includes the one in which the hydrogen atom bonded on the nitrogen atom in the ring is converted into methyl or ethyl.

Each of the monoalkylamino and the dialkylamino may be amino which is substituted with one or the same or different two, respectively, alkyls having a carbon number of from 1 to 6 (synonymous with that as described above) or alkyls having a carbon number of from 1 to 6 (synonymous with that as described above) substituted with amino, methylamino, ethylamino, dimethylamino, diethylamino, pyrrolidinyl, piperidyl, or morpholinyl. Examples thereof include methylamino, ethylamino, propylamino, butylamino, pentylamino, hexylamino, dimethylamino, diethylamino, ethylmethylamino, methylpropylamino, butylmethylamino, methylpentylamino, hexylmethylamino, aminoethylamino, aminopropylamino, (aminoethyl)methylamino, and bis(aminoethyl)amino. Of these, methylamino, ethylamino, dimethylamino, diethylamino, aminopropylamino, and bis(aminoethyl)amino, and the like are preferable.

In Compound (I), the amino, the monoalkylamino, and the dialkylamino may form an ammonio, a monoalkylammonio, and a dialkylammonio, respectively through coordination of a hydrogen ion to a lone pair on the nitrogen atom. The amino, the monoalkylamino, and the dialkylamino include the ammonio, the monoalkylammonio, and the dialkylammonio, respectively.

The trialkylammonio may be an ammonio substituted with three substituents, which are, the same or different, alkyl having 1 to 6 carbon atoms (having the same definition as described above), and alkyl having 1 to 6 carbon atoms (having the same definition as described above) substituted with amino, methylamino, ethylamino, dimethylamino, diethylamino, pyrrolidinyl, piperidyl or morpholinyl. Examples thereof include trimethylammonio, ethyldimethylammonio, diethylmethylammonio, triethylammonio, tripropylammonio, tributylammonio, tripentylammonio, trihexylammonio, tris(aminoethyl)ammonio, (aminoethyl)dimethylammonio, bis(aminoethyl)methylammonio, and the like. Preferred examples thereof include trimethylammonio, triethylammonio, tris(aminoethyl)ammonio, (aminoethyl)dimethylammonio, bis(aminoethyl)methylammonio, and the like.

In Compound (I), the ammonio, monoalkylammonio, and dialkylammonio in which a hydrogen ion coordinates to a lone pair on the nitrogen atom of the amino, monoalkylamino, and dialkylamino, respectively, and the trialkylammonio may form salts with pharmaceutically acceptable anions (having the same definitions as described above).

The alkoxy may be hydroxy which is substituted with alkyl having a carbon number of from 1 to 6 (synonymous with that as described above) or alkyl having a carbon number of from 1 to 6 (synonymous with that as described above) substituted with amino, methylamino, ethylamino, dimethylamino, diethylamino, pyrrolidinyl, piperidyl, or morpholinyl. Examples thereof include methoxy, ethoxy, propyloxy, butyloxy, pentyloxy, hexyloxy, aminoethoxy, and methylaminoethoxy. Of these, methoxy, ethoxy, aminoethoxy, methylaminoethoxy, and the like are preferable.

Each of the monoalkylcarbamoyl and the dialkylcarbamoyl may be carbamoyl which is substituted with one or the same or different two, respectively, alkyls having a carbon number of from 1 to 6 (synonymous with that as described above) or alkyls having a carbon number of from 1 to 6 (synonymous with that as described above) substituted with amino, methylamino, ethylamino, dimethylamino, diethylamino, pyrrolidinyl, piperidyl, or morpholinyl. Examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, aminoethylcarbamoyl, aminopropylcarbamoyl, (aminoethyl)methylcarbamoyl, and bis(aminoethyl)carbamoyl. Of these, methylcarbamoyl, ethylcarbamoyl, dimethylcarbamoyl, and the like are preferable.

In addition, it is more preferable that $X^1$ and $X^2$ are hydrogen atoms. In that case, $R^1$ and $R^2$, which are the same or different, are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl, and more preferably these are the same or different, (Z)-tetradec-7-enyl, (Z)-hexadec-7-enyl, (7Z,10Z)-hexadec-7,10-dienyl, or (9Z,12Z)-octadec-9,12-dienyl, and most preferably these are identically (Z)-tetradec-7-enyl, (Z)-hexadec-7-enyl, (7Z,10Z)-hexadec-7,10-dienyl, or (9Z,12Z)-octadec-9,12-dienyl.

Incidentally, when $X^1$ and $X^2$ are hydrogen atoms, then $R^3$ is more preferably a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl; still more preferably a hydrogen atom, methyl, or alkyl having a carbon number of from 1 to 6 or alkenyl having a carbon number of from 3 to 6, each substituted with 1 to 3 substituent(s), which is(are), the same or different, amino, hydroxy or carbamoyl; and most preferably a hydrogen atom or methyl.

In addition, when $X^1$ and $X^2$ are combined together to form a single bond or alkylene, then $R^1$ and $R^2$, which are the same or different, are each preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-1'-enyl or (11Z,14Z)-icosa-11,14-dienyl; more preferably (Z)-octadec-9-enyl or (9Z,12Z)-octadeca-9,12-dienyl; and most preferably these are identically (Z)-tetradec-7-enyl, (Z)-hexadec-7-enyl, (7Z,10Z)-hexadec-7,10-dienyl, or (9Z,12Z)-octadec-9,12-dienyl.

In addition, when $X^1$ and $X^2$ are combined together to form a single bond or alkylene, then $R^3$ is more preferably a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl; still more preferably a hydrogen atom, methyl, or alkyl having a carbon number of from 1 to 6 or alkenyl having a carbon number of from 3 to 6, each substituted with 1 to 3 substituent(s), which is(are), the same or different, amino, hydroxy or carbamoyl; and most preferably a hydrogen atom or methyl.

In addition, it is also one of more preferred embodiments of the present invention that when $X^1$ and $X^2$ are combined together to form a single bond, then $L^1$ is —CO— or —CO—O—. In that case, $R^3$ is still more preferably aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl, 2-carbamoylethyl, or the like, and most preferably 1,2-diaminoethyl, 1,3-diaminopropyl, 1,4-diaminobutyl or 1,5-diaminopentyl; and $R^1$ and $R^2$, which are the same or different, are each preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-1'-enyl or (11Z,14Z)-icosa-11,14-dienyl, more preferably (Z)-octadec-9-enyl or (9Z,12Z)-octadeca-9,12-dienyl, and most preferably these are identically (Z)-tetradec-7-enyl, (Z)-hexadec-7-enyl, (7Z,10Z)-hexadec-7,10-dienyl, or (9Z,12Z)-octadec-9,12-dienyl.

In addition, it is also one of more preferred embodiments of the present invention that when $X^1$ and $X^2$ are combined together to form a single bond, then $X^3$ is alkyl having 1 to 6 carbon atoms or alkenyl having 3 to 6 carbon atoms, and preferably methyl.

Incidentally, $L^1$ is more preferably a single bond. In addition, when $L^1$ is a single bond, then $R^3$ is more preferably a hydrogen atom, methyl, pyrrolidin-3-yl, piperidin-3-yl, piperidin-4-yl, or alkyl having a carbon number of from 1 to 6 or alkenyl having a carbon number of from 3 to 6, each substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl; still more preferably a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl, 1-methylpiperidin-4-yl, or the like; and most preferably a hydrogen atom or methyl.

In addition, when $L^1$ is —CO— or —CO—O—, then $R^3$ is more preferably pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, amino, monoalkylamino, dialkylamino, trialkylammonio, hydroxy, alkoxy, carbamoyl, monoalkylcarbamoyl, dialkylcarbamoyl, pyrrolidinyl, piperidyl or morpholinyl, wherein at least one of the substituents is amino, monoalkylamino, dialkylamino, trialkylammonio, pyrrolidinyl, piperidyl or morpholinyl; still more preferably aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, dimethylamino)propyl, 1-hydroxy-2-aminoethyl, 1-amino-2-hydroxyethyl, or the like; and most preferably 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, or the like.

In addition, $X^3$ is more preferably absent or is methyl, and still more preferably absent. When $X^3$ is methyl, then $R^3$ is more preferably methyl.

Incidentally, it is also one of preferred embodiments of the present invention that $X^3$ is absent, $Y^1$ is also absent, $L^1$ is a single bond, and $R^3$ is a hydrogen atom. In that case, $R^1$ and $R^2$, which are the same or different, are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl, and more preferably these are the same or different, (Z)-tetradec-7-enyl, or (7Z,10Z)-hexadec-7,10-dienyl, most preferably these are identically (Z)-tetradec-7-enyl, most preferably these are identically (Z)-hexadec-7-enyl, and most preferably these are identically (7Z,10Z)-hexadec-7,10-dienyl.

In addition, it is also one of preferred embodiments of the present invention that $X^3$ is absent, $Y^1$ is also absent, l2 is a single bond, and $R^3$ is methyl. In that case, $R^1$ and $R^2$, which are the same or different, are each preferably dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl, and more preferably these are the same or different, (Z)-tetradec-7-enyl, (7Z,10Z)-hexadec-7,10-dienyl, or (9Z,12Z)-octadec-9,12-dienyl, most preferably these are identically (Z)-tetradec-7-enyl, most preferably these are identically (7Z,10Z)-hexadec-7,10-dienyl, and most preferably these are identically (9Z,12Z)-octadec-9,12-dienyl.

Production methods of Compound (I) are described below. Incidentally, in the following production methods, in the case where the defined group or groups change under the conditions of the production method or are impertinent for carrying out the production method, the target compound can be produced by adopting common introduction and removal methods of a protective group in synthetic organic chemistry [for example, a method described in *Protective Groups in Organic Synthesis*, Third Edition, T. W. Greene, John Wiley & Sons Inc. (1999), etc.]. In addition, if desired, the order of reaction steps such as introduction of a substituent can be altered.

Production Method 1

In the Compound (I), Compound (Ia) in which $X^1$ and $X^2$ are hydrogen atom, $L^1$ is a single bond, and $X^3$ and $Y^1$ are absent can be produced by the following method.

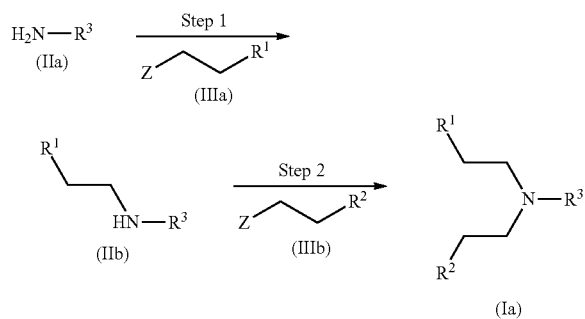

(In the formula, $R^1$, $R^2$ and $R^3$ have the same definitions as described above, respectively, and Z represents a leaving group such as a chlorine atom, a bromine atom, an iodine atom, trifluoromethanesulfonyloxy, methanesulfonyloxy, benzenesulfonyloxy, and p-toluenesulfonyloxy.)

Steps 1 and 2

Compound (IIb) can be produced by reacting Compound (IIa) and Compound (IIIa) in the absence or presence of a solvent and optionally in the presence of bases in an amount of preferably from 1 to 10 equivalents at a temperature between room temperature and 200° C. for from 5 minutes to 100 hours. Further, Compound (Ia) can be produced by reacting Compound (IIb) and Compound (IIIb) in the absence or presence of a solvent and optionally in the presence of bases in an amount of preferably from 1 to 10 equivalents at a temperature between room temperature and 200° C. for from 5 minutes to 100 hours, followed by isolation.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, and water. These solvents are used solely or in combination.

Examples of the base include potassium carbonate, potassium hydroxide, sodium hydroxide, sodium methoxide, potassium tert-butoxide, triethylamine, diisopropylethylamine, N-methylmorpholine, pyridine, and 1,8-diazabicyclo[5.4.0]-7-undecene (DBU).

Compound (IIa) can be obtained as a commercially available product or by a known method (for example, Dai 5-han, *Jikken Kagaku Kouza* (5th edition, Courses in Experimental Chemistry) 14, "Synthesis of Organic Compounds II", 5th edition, p. 351, Maruzen (2005)) or a method similar thereto.

Each of Compound (IIIa) and Compound (IIIb) can be obtained as a commercially available product or by a known method (for example, Dai 5-han, *Jikken Kagaku Kouza* (5th edition, Courses in Experimental Chemistry) 13, "Synthesis of Organic Compounds I", 5th edition, p. 374, Maruzen (2005)) or a method similar thereto.

Compound (Ia) in the case where $R^1$ and $R^2$ are identical can be obtained using 2 equivalents or more of Compound (IIIa) in Step 1.

Production Method 2

In the Compound (I), Compound (Ib) in which $X^1$ and $X^2$ are combined together to form a single bond or alkyleneO-, $L^1$ is a single bond, and $X^3$ and $Y^1$ are absent can be produced by the following method.

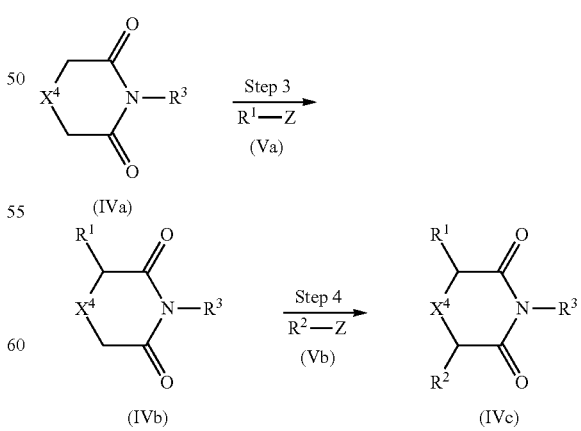

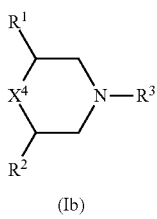

(Ib)

(In the formula, $R^1$, $R^2$, $R^3$ and Z have the same definitions as described above, respectively, and $X^4$ represents a single bond or alkylene.)

Steps 3 and 4

Compound (IVb) can be produced by reacting Compound (IVa) and Compound (Va) in the presence of a solvent and in the presence of bases in an amount of preferably from 1 to 10 equivalents at temperature between −100° C. and 100° C. for from 5 minutes to 100 hours. Further, Compound (IVc) can be produced by reacting Compound (IVb) and Compound (Vb) in the absence or presence of a solvent and optionally in the presence of bases in an amount of preferably from 1 to 10 equivalents at a temperature between −100° C. and 100° C. for from 5 minutes to 100 hours, followed by isolation.

The same solvents used in production method 1 may be used.

Examples of the base include sodium hydroxide, potassium hydroxide, potassium tert-butoxide, sodium tert-butoxide, lithium diisopropylamide (LDA), and lithium hexamethyldisilazide (LHMDS).

Compound (IVa) can be obtained as a commercially available product or by a known method (for example, Dai 5-han, *Jikken Kagaku Kouza* (5th edition, Courses in Experimental Chemistry) 14, "Synthesis of Organic Compounds II", 5th edition, p. 146, Maruzen (2005)) or a method similar thereto.

Each of Compound (Va) and Compound (Vb) can be obtained as a commercially available product or by a known method (for example, Dai 5-han, *Jikken Kagaku Kouza* (5th edition, Courses in Experimental Chemistry) 13, "Synthesis of Organic Compounds I", 5th edition, p. 374, Maruzen (2005)) or a method similar thereto.

Compound (IVc) in the case where $R^1$ and $R^2$ are identical can be obtained using 2 equivalents or more of Compound (Va) in Step 3.

Step 5

Compound (Ib) can be produced by reacting Compound (IVc) in a solvent at a temperature between −100° C. and 100° C. for 5 minutes to 100 hours in the presence of 1 to large excess amounts of a reducing agent, and, if necessary, preferably 0.1 to 10 equivalents of a metallic compound.

Examples of the reducing agent include lithium aluminum hydride, sodium borohydride, sodium triacetoxyborohydride, sodium cyanoborohydride, and the like.

Examples of the metallic compound include cobalt chloride, iron chloride, aluminum chloride, and the like.

Production Method 3

In Compound (I), Compound (Ic) in which $L^1$ is a single bond, $R^3$ is —$CHR^AR^B$ (in the formula, $R^A$ and $R^B$, which are the same or different, are each a hydrogen atom, alkyl having a carbon number of from 1 to 5, alkenyl having a carbon number of from 2 to 5, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 5 or alkenyl having a carbon number of from 2 to 5, each substituted with the same or different one to three of amino, monoalkylamino, dialkylamino, trialkylammonio, hydroxy, alkoxy, carbamoyl, monoalkylcarbamoyl, dialkylcarbamoyl, pyrrolidinyl, piperidyl, or morpholinyl, or taken together with the adjacent carbon atom to form pyrrolidin-3-yl, piperidin-3-yl, or piperidin-4-yl; a total sum of the carbon number of each of the alkyl, the alkyl moiety of the substituted alkyl, the alkenyl, and the alkenyl moiety of the substituted alkenyl in $R^A$ and $R^B$ is from 1 to 5, except the case where $R^A$ and $R^B$ are each a hydrogen atom; in the case where either $R^A$ or $R^B$ is pyrrolidin-2-yl, pyrrolidin-3-yl, piperidin-2-yl, piperidin-3-yl, piperidin-4-yl, morpholin-2-yl, or morpholin-3-yl, the other $R^A$ or $R^B$ is a hydrogen atom, alkyl having a carbon number of from 1 to 5, alkenyl having a carbon number of from 2 to 5, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 5 or alkenyl having a carbon number of from 3 to 5, each substituted with the same or different one or two of amino, monoalkylamino, dialkylamino, trialkylammonio, hydroxy, alkoxy, carbamoyl, monoalkylcarbamoyl, dialkylcarbamoyl, pyrrolidinyl, piperidyl, or morpholinyl; and in the case where $R^A$ and $R^B$ are each substituted alkyl or alkenyl, a total sum of the number of the substituents is 2 or 3); and $X^3$ and $Y^1$ are absent can be produced in the following method.

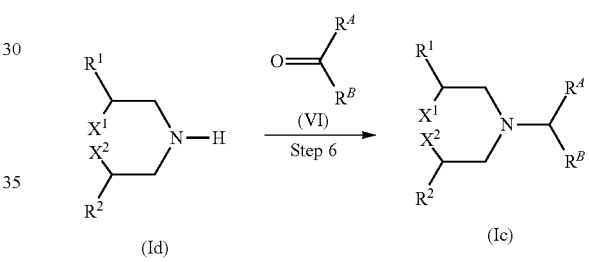

In the foregoing formulae, $R^1$, $R^2$, $R^A$, $R^B$, $X^1$ and $X^2$ are synonymous with those as described above, respectively.

Step 6

Compound (Ic) can be produced by allowing Compound (Id) in which $R^3$ in Compound (Ia) and compound (Ib) is a hydrogen atom to react with Compound (VI) in an amount of preferably from 1 to 10 equivalents in a solvent in the presence of a reducing agent in an amount of preferably from 1 equivalent to a large excess and optionally an acid in an amount of preferably from 1 to 10 equivalents at a temperature between −20° C. and 150° C. for from 5 minutes to 72 hours.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and water. These solvents are used solely or in combination.

Examples of the reducing agent include sodium triacetoxyborohydride and sodium cyanoborohydride.

Examples of the acid include hydrochloric acid and acetic acid.

Compound (VI) can be obtained as a commercially available product or by a known method (for example, Dai 5-han, *Jikken Kagaku Kouza* (5th edition, Courses in Experimental Chemistry) 15, "Synthesis of Organic Compounds III", 5th edition, p. 1, Maruzen (2005); and Dai 5-han, *Jikken Kagaku Kouza* (5th edition, Courses in Experimental Chemistry) 15, "Synthesis of Organic Compounds III", 5th edition, p. 153, Maruzen (2005)) or a method similar thereto.

Production Method 4

In Compound (I), Compound (Ie) in which $L^1$ is —CO—, and $X^3$ and $Y^1$ are absent can be produced by the following method.

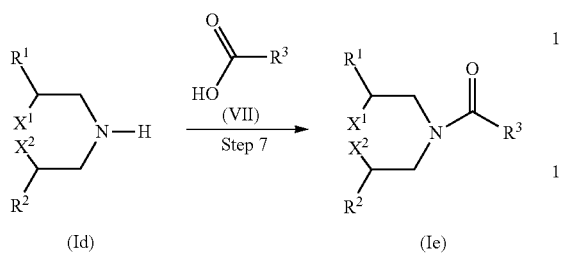

(In the formula, $R^1$, $R^2$, $R^3$, $X^1$ and $X^2$ have the same definitions as described above, respectively.)

Step 7

Compound (Ie) can be produced by treating Compound (Id) and Compound (VII) in a solvent at a temperature between −20° C. and 150° C. for 5 minutes to 100 hours in the presence of 1 equivalent to large excess amounts of a condensing agent. If necessary, preferably 0.01 to 10 equivalents of an additive, and/or preferably 1 to large excess amounts of a base may be added to promote the reaction.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, dimethylsulfoxide, water, and the like. These may be used either alone or as a mixture.

Examples of the condensing agent include 1,3-dicyclohexylcarbodiimide, 1-ethyl-3-(3-dimethylaminopropyl)carbodiimide.hydrochloride, carbonyldiimidazole, benzotriazol-1-yloxytris(dimethylamino)phosphonium hexafluorophosphate, (benzotriazol-1-yloxy)tripyrrolizinophosphonium hexafluorophosphate, O-(7-azabenzotriazol-1-yl)-N,N,N',N'-tetramethyluronium hexafluorophosphate, O-(benzotriazol-1-yl)-N,N,N',N'-tetramethyluronium hexafluorophosphate, 2-chloro-1-methylpyridinium iodide, and the like.

Examples of the additive include 1-hydroxybenzotriazole, 4-dimethylaminopyridine, and the like.

Examples of the base include potassium acetate, sodium bicarbonate, potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene, and the like.

Compound (VII) can be obtained as a commercially available product or by known methods (for example, Dai 5-han, *Jikken Kagaku Kouza* (5th edition, *Courses in Experimental Chemistry*) 16, *Synthesis of Organic Compounds IV*, 5th Ed., p. 1, Maruzen (2005)), or a method in conformity thereof.

Production Method 5

In Compound (I), Compound (If) in which $L^1$ is —CO—O—, and $X^3$ and $Y^1$ are absent can be produced by the following methods.

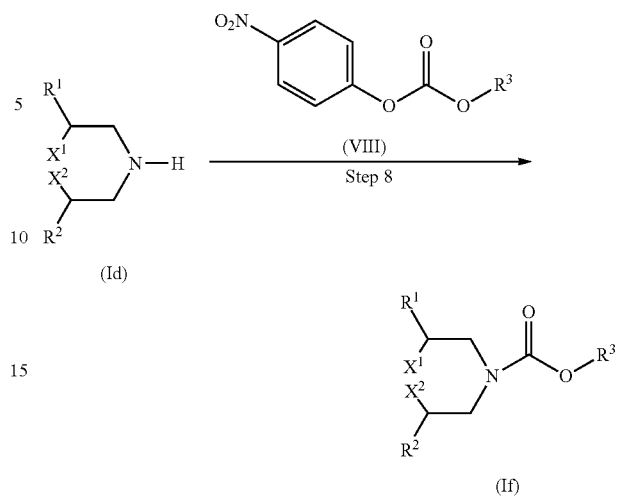

(In the formula, $R^1$, $R^2$, $R^3$, $X^1$ and $X^2$ have the same definitions as described above, respectively.)

Step 8

Compound (If) can be produced by reacting Compound (Id) with Compound (VIII) without solvent or in a solvent at a temperature between −20° C. and 150° C. for 5 minutes to 72 hours, in the presence of preferably 1 to 10 equivalents of an additive, and/or preferably 1 to 10 equivalents of a base, if necessary.

The same solvents and additives used in production method 4 may be used.

Examples of the base include triethylamine, diisopropylethylamine, N-methylmorpholine, pyridine, 1,8-diazabicyclo[5.4.0]-7-undecene, and the like.

Compound (VIII) can be obtained as a commercially available product or by known methods (for example, Journal of American Chemical Society (J. Am. Chem. Soc.), 1981, Vol. 103, p. 4194-4199), or a method in conformity thereof.

Production Method 6

In Compound (I), Compound (Ig) in which $L^1$ is a single bond, $R^3$ is —$CH_2$—$C(OH)R^CR^D$ (in the formula, $R^C$ and $R^D$, which are the same or different, are each a hydrogen atom, alkyl having a carbon number of from 1 to 4, alkenyl having a carbon number of from 2 to 4, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 4 or alkenyl having a carbon number of from 2 to 4, each substituted with the same or different one or two of amino, monoalkylamino, dialkylamino, trialkylammonio, hydroxy, alkoxy, carbamoyl, monoalkylcarbamoyl, dialkylcarbamoyl, pyrrolidinyl, piperidyl, or morpholinyl; a total sum of the carbon number of each of the alkyl, the alkyl moiety of the substituted alkyl, the alkenyl, and the alkenyl moiety of the substituted alkenyl in $R^C$ and $R^D$ is from 1 to 4 except the case where $R^C$ and $R^D$ are each a hydrogen atom; in the case where either $R^C$ or $R^D$ is pyrrolidin-2-yl, pyrrolidin-3-yl, piperidin-2-yl, piperidin-3-yl, piperidin-4-yl, morpholin-2-yl, or morpholin-3-yl, the other $R^C$ or $R^D$ is a hydrogen atom, alkyl having a carbon number of from 1 to 4, alkenyl having a carbon number of from 2 to 4, pyrrolidin-2-yl, pyrrolidin-3-yl, piperidin-2-yl, piperidin-3-yl, piperidin-4-yl, morpholin-2-yl, morpholin-3-yl, or alkyl having a carbon number of from 1 to 4 or alkenyl having a carbon number of from 2 to 4, each substituted with one amino, monoalkylamino, dialkylamino, trialkylammonio, hydroxy, alkoxy, carbamoyl, monoalkylcarbamoyl, dialkylcarbamoyl, pyrrolidinyl, piperidyl, or morpholinyl; and in the case where $R^C$ and $R^D$ are each a substituted alkyl or alkenyl, a total sum of the number of the substituents is 2), and $X^3$ and $Y^1$ are absent can be produced in the following method.

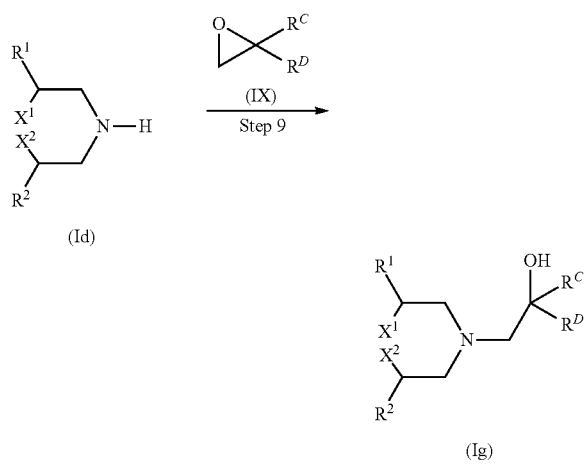

(Id)

(Ig)

In the foregoing formulae, $R^1$, $R^2$, $R^C$, $R^D$, $X^1$ and $X^2$ are synonymous with those as described above, respectively.

Step 9

Compound (Ig) can be produced by reacting Compound (Id) and Compound (IX) in the absence or presence of a solvent at a temperature between 0° C. and 230° C. for from 5 minutes to 100 hours.

Examples of the solvent include methanol, ethanol, 1-propanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, and dimethyl sulfoxide. These solvents are used solely or in combination.

Compound (IX) can be obtained as a commercially available product or by a known method (for example, Dai 5-han, *Jikken Kagaku Kouza* (5th edition, Courses in Experimental Chemistry) 17, "Synthesis of Organic Compounds V", 5th edition, p. 186, Maruzen (2005)) or a method similar thereto.

Production Method 7

In Compound (I), Compound (Ih) in which $L^1$ is a single bond, $X^3$ is alkyl having 1 to 6 carbon atoms or alkenyl having 3 to 6 carbon atoms, and $Y^1$ is a pharmaceutically acceptable anion can be produced by the following method.

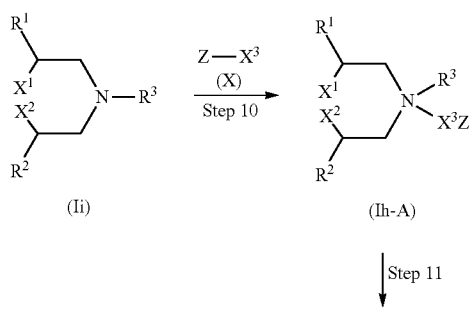

-continued

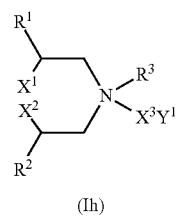

(Ih)

(In the formula, $R^1$, $R^2$, $R^3$, $X^1$, $X^2$, $X^3$, $Y^1$ and Z have the same definitions as described above, respectively.)

Steps 10 and 11

Compound (Ii) is Compound (Ia) or Compound (Ib).

Compound (Ih-A) can be produced by treating Compound (Ii) and Compound (X) in a solvent or without solvent at a temperature between 0° C. and 230° C. for 5 minutes to 100 hours. Compound (Ih) can be produced by treating Compound (Ih-A) with Y-type anion-exchange resin.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, and the like. These may be used either alone or as a mixture.

Compound (X) can be obtained as a commercially available product or by known methods (for example, Dai 5-han, *Jikken Kagaku Kouza* (5th edition, *Courses in Experimental Chemistry*) 13, *Synthesis of Organic Compounds I*, 5th Ed., p. 374, Maruzen (2005)), or a method in conformity thereof.

When Z and $Y^1$ are identical, Compound (Ih) may be produced by omitting step 11.

Conversion of the functional groups contained in $R^1$, $R^2$, and $R^3$ in Compound (I) can also be carried out by a known method [for example, a method described in *Comprehensive Organic Transformations* 2nd edition, written by R. C. Larock, Vch Verlagsgesellschaft Mbh (1999), etc.] or a method similar thereto.

The intermediate and the target compound in each of the foregoing production methods can be isolated and purified by means of a separation and purification method which is commonly adopted in the synthetic organic chemistry, for example, filtration, extraction, washing, drying, concentration, recrystallization, a variety of chromatography, etc. In addition, in the intermediate, it is also possible to subject it to the subsequent reaction without being particularly purified.

In Compound (I), a hydrogen ion may coordinate to a lone pair on the nitrogen atom in the structure, and the nitrogen atom may form a salt together with a pharmaceutically acceptable anion (having the same definition as described above). Compound (I) encompass compounds in which a hydrogen ion coordinates to a lone pair on the nitrogen atom. Note that, in the present invention, the absence of $X^3$ encompasses the case where a hydrogen ion is coordinated.

In Compounds (I), there may exist compounds in which stereoisomer such as geometrical isomers and optical isomers, tautomers, and the like. Compounds (I) include all of possible isomers and mixtures thereof inclusive of the foregoing stereoisomers and tautomers.

A part or all of the respective atoms in Compounds (I) may be substituted with a corresponding isotope atom. Compounds (I) include compounds in which a part or all of the respective atoms thereof are substituted with those isotope atoms. For example, a part or all of hydrogen atoms in each of Compounds (I) may be a hydrogen atom having an atomic weight of 2 (heavy hydrogen atom).

The compounds in which a part of or all of the atoms in Compound (I) are replaced with corresponding isotope atoms can be produced by using methods similar to the foregoing production methods, using commercially available building blocks. Further, the compounds in which a part of or all of the hydrogen atoms in Compound (I) are replaced with deuterium atoms can be synthesized by using various methods, including, for example, (1) a method in which a carboxylic acid or the like is deuterated using deuterium peroxide under a basic condition (see U.S. Pat. No. 3,849,458), (2) a method in which an alcohol, a carboxylic acid, or the like is deuterated using an iridium complex as a catalyst and using heavy water as a deuterium source (see J. Am. Chem. Soc., Vol. 124, No. 10, 2092 (2002)), (3) a method in which a fatty acid is deuterated using palladium-carbon as a catalyst and using only a deuterium gas as a deuterium source (see LIPIDS, Vol. 9, No. 11, 913 (1974)), (4) a method in which acrylic acid, methyl acrylate, methacrylic acid, methyl methacrylate, or the like is deuterated using a metal such as platinum, palladium, rhodium, ruthenium, and iridium as a catalyst and using heavy water or heavy water and a deuterium gas as a deuterium source (see Japanese Published Examined Patent Application No. 19536/1993, and Japanese Published Unexamined Patent Application No. 277648/1986 and No. 275241/1986), and (5) a method in which acrylic acid, methyl methacrylate, or the like is deuterated using a catalyst such as palladium, nickel, copper, and copper chromite and using heavy water as a deuterium source (see Japanese Published Unexamined Patent Application No. 198638/1988), and the like.

Specific examples of Compound (I) are shown in Table 1. However, it should not be construed that Compound (I) in the present invention are limited thereto.

In addition, the nucleic acid as a drug to be used in the present invention may be any molecule so far as it is a molecule obtained through polymerization of nucleotides and/or molecules having an equal function to the nucleotide. Examples thereof include RNA that is a polymer of ribonucleotides; DNA that is a polymer of deoxyribonucleotides; a chimera nucleic acid composed of RNA and DNA; and a nucleotide polymer in which at least one nucleotide in these nucleic acids is substituted with a molecule having an equal function to the nucleotide. In addition, a derivative containing at least one molecule obtained through polymerization of nucleotides and/or molecule having an equal function to the nucleotide as a building block is also included in the nucleic acid of the present invention. In addition, Examples thereof include a peptide nucleic acid (PNA) [Acc. Chem. Res., 32, 624 (1999)], an oxy-peptide nucleic acid (OPNA) [J. Am. Chem. Soc., 123, 4653 (2001)], a peptide ribonucleic acid (PRNA) [J. Am. Chem. Soc., 122, 6900 (2000)]. Incidentally, in the present invention, uridine U in RNA and thymine T in DNA can be deemed to be replaced with each other.

Examples of the molecule having an equal function to the nucleotide include nucleotide derivatives.

The nucleotide derivative may be any molecule so far as it is a molecule obtained by applying modification to the nucleotide. For example, for the purpose of enhancing the nuclease resistance or achieving stabilization from other decomposing factor(s) as compared with RNA or DNA, increasing the affinity to the complementary strand nucleic acid, increasing the cellular permeability, or achieving the visualization, molecules obtained by applying modification to ribonucleotide(s) or deoxyribonucleotide(s) are suitably used.

Examples of the nucleotide derivative include a sugar moiety modified nucleotide, a phosphodiester bond modified nucleotide, and a base modified nucleotide.

The sugar moiety modified nucleotide may be any nucleotide in which a part or the entirety of the chemical structure of the sugar moiety of the nucleotide is modified or substituted with an arbitrary substituent, or substituted with an arbitrary atom. Above all, a 2'-modified nucleotide is preferably used.

TABLE 1

| Compound No. | Structure |
|---|---|
| 1 | 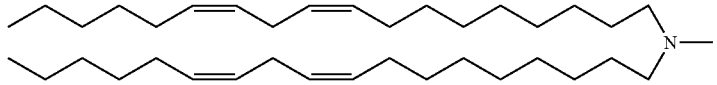 |
| 2 | 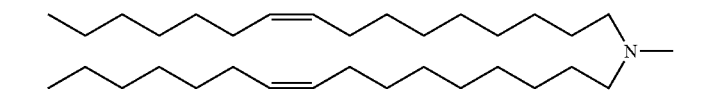 [SMILES: CCCCCC/C=C\CCCCCCCCN(C)CCCCCCCC/C=C\CCCCCC] |
| 3 | 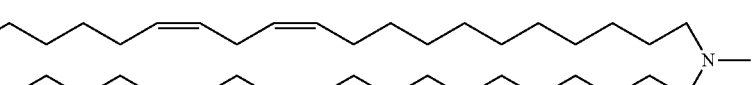 |
| 4 | 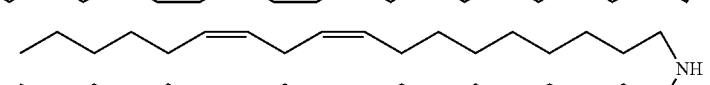 |
| 5 | 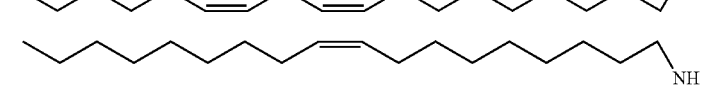 |
| 6 | 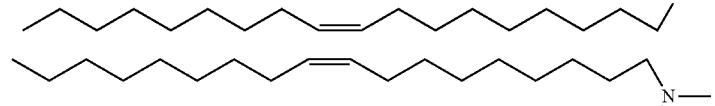 |

Examples of the modifying group in the sugar moiety modified nucleotide include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'—SiH$_2$-substituted alkyl, 2'-ONO$_2$, 2'NO$_2$, 2'-N$_3$, 2'-amino acid residue (amino acid with the hydroxyl group removed from the carboxylic acid), and 2'-β-amino acid residue (having the same definition as above), and the like. The nucleotide with the substitution by a modifying group at 2' position in the present invention also encompasses bridged nucleic acids (BNAs) having a structure in which the modifying group at 2' position is bridged to the 4' carbon atom, specifically, locked nucleic acids (LNAs) in which the oxygen atom at 2' position is bridged to the 4' carbon atom via methylene, ethylene bridged nucleic acids (ENAs) [Nucleic Acid Research, 32, e175 (2004)], and the like.

The preferred modifying group in the sugar moiety modified nucleotide include 2'-cyano, 2'-halogen, 2'-O-cyano, 2'-alkyl, 2'-substituted alkyl, 2'-O-alkyl, 2'-O-substituted alkyl, 2'-β-alkenyl, 2'-O-substituted alkenyl, 2'-Se-alkyl, 2'-Se-substituted alkyl, and the like. More preferred examples include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-(2-[N,N-dimethyl]aminooxy)ethyl, 2'-O-[3-(N,N-dimethylamino)propyl], 2'-0-[2-[2-(N,N-dimethylamino)ethoxy]ethyl], 2'-O-[2-(methylamino)-2-oxoethyl], and 2'-Se-methyl. Even more preferred are 2'-O-methyl, 2'-O-ethyl, 2'-fluoro, and the like. 2'-O-methyl and 2'-O-ethyl are most preferable.

The preferred range of the modifying group in the sugar moiety modified nucleotide may also be defined based on its size. Modifying groups of a size corresponding to the size of fluoro to the size of —O-butyl are preferable, and modifying groups of a size corresponding to the size of —O-methyl to the size of —O-ethyl are more preferable.

The alkyl in the modifying group of the sugar moiety modified nucleotide is synonymous with the alkyl having a carbon number of from 1 to 6 in Compound (I).

The alkenyl in the modifying group of the sugar moiety modified nucleotide is synonymous with the alkenyl having a carbon number of from 3 to 6 in Compound (I).

Examples of the halogen in the modifying group of the sugar moiety modified nucleotide include a fluorine atom, a chlorine atom, a bromine atom, and an iodine atom.

Examples of the amino acid in the amino acid residue include aliphatic amino acids (specifically, glycine, alanine, valine, leucine, isoleucine, and the like), hydroxy amino acids (specifically, serine, threonine, and the like), acidic amino acids (specifically, aspartic acid, glutamic acid, and the like), acidic amino acid amides (specifically, asparagine, glutamine, and the like), basic amino acids (specifically, lysine, hydroxylysine, arginine, ornithine, and the like), sulfur-containing amino acids (specifically, cysteine, cystine, methionine, and the like), imino acids (specifically, proline, 4-hydroxy proline, and the like), and the like.

Examples of the substituent in the substituted alkyl and the substituted alkenyl in the sugar moiety modified nucleotide include halogen (having the same definition as above), hydroxy, sulfanyl, amino, oxo, —O-alkyl (the alkyl moiety of the —O-alkyl has the same definition as above), —S-alkyl (the alkyl moiety of the —S-alkyl has the same definition as above), —NH-alkyl (the alkyl moiety of the —NH-alkyl has the same definition as above), dialkylaminooxy (the two alkyl moieties of the dialkylaminooxy may be the same or different, and have the same definition as above), dialkylamino (the two alkyl moieties of the dialkylamino may be the same or different, and have the same definition as above), dialkylaminoalkyleneoxy (the two alkyl moieties of the dialkylaminoalkyleneoxy may be the same or different, and have the same definition as above; the alkylene means a group wherein the one hydrogen atom is removed from the above-defined alkyl), and the like, and the number of the substituent is preferably 1 to 3.

The phosphodiester bond modified nucleotide may be any nucleotide in which a part or the entirety of the chemical structure of the phosphodiester bond of the nucleotide is modified or substituted with an arbitrary substituent, or substituted with an arbitrary atom. Examples thereof include a nucleotide in which the phosphodiester bond is substituted with a phosphorothioate bond, a nucleotide in which the phosphodiester bond is substituted with a phosphorodithioate bond, a nucleotide in which the phosphodiester bond is substituted with an alkylphosphonate bond, and a nucleotide in which the phosphodiester bond is substituted with a phosphoroamidate bond.

The base modified nucleotide may be any nucleotide in which a part or the entirety of the chemical structure of the base of the nucleotide is modified or substituted with an arbitrary substituent, or substituted with an arbitrary atom. Examples thereof include a nucleotide in which an oxygen atom in the base is substituted with a sulfur atom, a nucleotide in which a hydrogen atom is substituted with an alkyl group having a carbon number of from 1 to 6, a nucleotide in which a methyl group is substituted with a hydrogen atom or an alkyl group having a carbon number of from 2 to 6, and a nucleotide in which an amino group is protected by a protective group such as an alkyl group having a carbon number of from 1 to 6 or an alkanoyl group having a carbon number of from 1 to 6.

Furthermore, examples of the nucleotide derivative include those in which other chemical substance(s) such as a lipid, a phospholipid, phenazine, folate, phenanthridine, anthraquinone, acridine, fluorescein, rhodamine, coumarin, and a pigment are added to the nucleotide or the nucleotide derivative in which at least one of the sugar moiety, the phosphodiester bond, and the base is modified. Specific examples thereof include 5'-polyamine added nucleotide derivatives, cholesterol added nucleotide derivatives, steroid added nucleotide derivatives, bile acid added nucleotide derivatives, vitamin added nucleotide derivatives, Cy5 added nucleotide derivatives, Cy3 added nucleotide derivatives, 6-FAM added nucleotide derivatives, and biotin added nucleotide derivatives.

In addition, the nucleotide derivatives may form, together with another nucleotide or nucleotide derivative within the nucleic acid, a crosslinked structure such as an alkylene structure, a peptide structure, a nucleotide structure, an ether structure, or an ester structure, or a structure which is a combination of at least one of these structures.

Examples of the nucleic acids used in the present invention include preferably nucleic acids that suppress the expression of the target gene, more preferably nucleic acids that have an activity of suppressing the expression of the target gene by utilizing RNA interference (RNAi).

The target gene used in the present invention is not particularly limited, as long as it is expressed through mRNA production. Preferred examples thereof include genes associated with tumor or inflammation, including, for example, genes that encodes proteins such as vascular endothelial growth factors (hereinafter, "VEGF"), vascular endothelial growth factor receptors (hereinafter, "VEGFR"), fibroblast growth factors, fibroblast growth factor receptors, platelet-derived growth factors, platelet-derived growth factor receptors, liver cell growth factors, liver cell growth factor receptors, Kruppel-like factors (hereinafter, "KLF"), Ets transcription factors, nuclear factors, hypoxia-inducible factors, cell cycle-related factors, chromosome replication-related factors, chromosome repair-related factors, microtubule-related factors, growth signaling pathway-related factors, growth-related transcription factors, and apoptosis-related factors. Specific examples thereof include VEGF genes, VEGFR genes, fibroblast growth factor genes, fibroblast growth factor receptor genes, platelet-derived growth factor genes, platelet-derived growth factor receptor genes, liver cell growth factor genes, liver cell growth factor receptor genes, KLF genes, Ets transcription factor genes, nuclear factor genes, hypoxia-inducible factor genes, cell cycle-related factor genes, chromosome replication-related factor genes, chromosome repair-related factor genes, microtubule-related factor genes (for example, CKAP5 genes and the like), growth signaling pathway-related factor genes, growth-related transcription factor genes (for example, KRAS genes and the like), and apoptosis-related factor genes (for example, BCL-2 genes and the like), and the like.

Preferably, the target gene used in the present invention is a gene that is expressed, for example, in liver, lungs, kidneys or spleen. Examples thereof include genes associated with tumor or inflammation (such as above), hepatitis B virus genome, hepatitis C virus genome, and genes that encode proteins such as apolipoprotein (APO), hydroxymethyl glutaryl (HMG) CoA reductase, kexin type 9 serine protease (PCSK9), factor XII, glucagon receptor, glucocorticoid receptor, leukotriene receptor, thromboxane A2 receptor, histamine H1 receptor, carbonic anhydrase, angiotensin converting enzyme, renin, p53, tyrosine phosphatase (PTP), sodium dependent glucose transporter, tumor necrosis factor, and interleukin, and the like.

The nucleic acid that suppresses the expression of the target gene may be any of, for example, double-stranded nucleic acids (such as siRNA (short interference RNA), and miRNA (micro RNA)), single-stranded nucleic acid (shRNA (short hairpin RNA), antisense nucleic acids, ribozyme, etc), and the like, provided that, for example, the nucleic acid contains a base sequence complementary to a part of the base sequence of the mRNA of the gene (target gene) encoding a protein and the like, and that the nucleic acid suppresses the expression of the target gene. Double-stranded nucleic acids are preferably used.

The nucleic acids that contain a base sequence complementary to a part of the base sequence of the target gene mRNA are also referred to as antisense strand nucleic acids, and the nucleic acids that contain a base sequence complementary to the base sequence of the antisense strand nucleic acid are also referred to as sense strand nucleic acids. The sense strand nucleic acids are nucleic acids that can form a double strand by pairing with antisense strand nucleic acids, including the nucleic acid itself that has a partial base sequence of the target gene.

The double-stranded nucleic acids are nucleic acids that have two strands forming a double-stranded portion by pairing. The double-stranded portion is a portion where a double strand is formed by the base pairing of the nucleotides or derivatives thereof forming a double-stranded nucleic acid. The base pairs forming the double-stranded portion are typically 15 to 27 bps, preferably 15 to 25 bps, more preferably 15 to 23 bps, further preferably 15 to 21 bps, particularly preferably 15 to 19 bps.

Preferred for use as the antisense strand nucleic acid of the double-stranded portion are nucleic acids that contain a partial sequence of the target gene mRNA, with or without the substitution, deletion, or addition of 1 to 3 bases, preferably 1 to 2 bases, more preferably 1 base, and that have a target protein expression suppressing activity. The length of the single-stranded nucleic acid forming a double-stranded nucleic acid is typically 15 to 30 bases, preferably 15 to 29 bases, more preferably 15 to 27 bases, further preferably 15 to 25 bases, particularly preferably 17 to 23 bases, most preferably 19 to 21 bases.

The nucleic acid in the antisense strand and/or the sense strand forming a double-stranded nucleic acid may have an additional nucleic acid that does not form a double strand, contiguous from the 3'-end or 5'-end of the double-stranded portion. Such portions not forming a double strand are also referred to as an extension (overhang).

The extension in such double-stranded nucleic acids has 1 to 4 bases, typically 1 to 3 bases at the 3'-end or 5'-end of at least one of the strands. Preferably, the extension has 2 bases, more preferably dTdT or UU. The extension may be present on only one of the antisense strand and the sense strand, or on both of the antisense strand and the sense strand. However, double-stranded nucleic acids having extensions on both the antisense strand and the sense strand are preferably used.

It is also possible to use a sequence contiguous from the double-stranded portion and partially or completely matches the target gene mRNA, or a sequence contiguous from the double-stranded portion and matches the base sequence of the complementary strand of the target gene mRNA. Further, the nucleic acid that suppresses the expression of the target gene may be, for example, a nucleic acid molecule that generates a double-stranded nucleic acid by the activity of a ribonuclease such as Dicer (WO2005/089287), or a double-stranded nucleic acid that does not have a 3' or 5' extension.

When the nucleic acid is siRNA, the antisense strand has a base sequence in which at least bases 1 to 17 from the 5'-end to the 3'-end are complementary to 17 contiguous bases of the target gene mRNA. Preferably, the antisense strand has a base sequence in which bases 1 to 19 from the 5'-end to the 3'-end are complementary to 19 contiguous bases of the target gene mRNA, a base sequence in which bases 1 to 21 are complementary to 21 contiguous bases of the target gene mRNA, or a base sequence in which bases 1 to 25 are complementary to 25 contiguous bases of the target gene mRNA.

Further, when the nucleic acid used in the present invention is siRNA, preferably 10 to 70%, more preferably 15 to 60%, further preferably 20 to 50% of the sugars in the nucleic acid are riboses substituted with a modifying group at the 2'-position. In the present invention, the substitution of the ribose with a modifying group at the 2'-position means the substitution of the hydroxyl group with a modifying group at the 2'-position. The configuration may be the same as or different from the configuration of the ribose hydroxyl group at the 2'-position. Preferably, the configuration is the same as the configuration of the ribose hydroxyl group at the 2'-position. The ribose substituted with a modifying group at the 2'-position is included within a 2'-modified nucleotide from among sugar-modified nucleotides, and the modifying group of the ribose substituted at the 2'-position has the same definition as the modifying group of 2'-modified nucleotides.

The nucleic acid used in the present invention includes derivatives in which the oxygen atom or the like contained in the phosphate moiety, the ester moiety, or the like in the structure of the nucleic acid is replaced with other atoms, for example, such as a sulfur atom.

In addition, in the sugar binding to the base at the 5'-end of each of the antisense strand and the sense strand, the hydroxyl group at the 5'-end may be modified with a phosphate group or the foregoing modifying group, or a group which is converted into a phosphate group or the foregoing modifying group by a nucleolytic enzyme or the like in a living body.

In addition, in the sugar binding to the base at the 3'-end of each of the antisense strand and the sense strand, the hydroxyl group at the 3'-end may be modified with a phosphate group or the foregoing modifying group, or a group which is converted into a phosphate group or the foregoing modifying group by a nucleolytic enzyme or the like in a living body.

The single-stranded nucleic acid may be any of nucleic acids that contain a sequence complementary to the contiguous 15 to 27 base sequence, preferably 15 to 25 base sequence, more preferably 15 to 23 base sequence, further preferably 15 to 21 base sequence, particularly preferably 15 to 19 base sequence of the target gene, with or without the substitution, deletion, or addition of 1 to 3 bases, preferably 1 to 2 bases, more preferably 1 base, and that have a target protein expression suppressing activity. Preferred for use is a single-stranded nucleic acid having 15 to at most 30 bases, preferably 15 to 29 bases, more preferably 15 to 27 bases, further preferably 15 to 25 bases, particularly preferably 15 to 23 bases.

The single-stranded nucleic acid may be one obtained by connecting the antisense strand and the sense strand of the double-stranded nucleic acid via a spacer sequence (supacer oligonucleotide). Preferred as the spacer oligonucleotide is a single-stranded nucleic acid molecule of 6 to 12 bases, with a UU sequence at the 5'-end. Examples of the spacer oligonucleotide contain a nucleic acid having the sequence UUCAAGAGA. Either the antisense strand or the sense strand joined by a spacer oligonucleotide may represent the 5'-end. Preferably, the single-stranded nucleic acid is a single-stranded nucleic acid, such as shRNA, that has a stem-loop structure with a double-stranded portion. Single-stranded nucleic acids such as shRNA are typically 50 to 70 bases long.

It is also possible to use nucleic acids at most 70 bases long, preferably at most 50 bases long, further preferably at most 30 bases long, designed to generate the single-stranded nucleic acid or the double-stranded nucleic acid by the activity of ribonuclease or the like.

In addition, the nucleic acids used in the present invention may be produced by using known RNA or DNA synthesis techniques, and RNA or DNA modification techniques.

The lipid nano particles in the present invention comprise Compound (I). Examples of the lipid nano particles include lipid nano particles comprising a complex of Compound (I) and a nucleic acid; lipid nano particles comprising a complex between a combination having Compound (I) with a neutral lipid and/or a polymer and a nucleic acid; and lipid nano particles constituted of the complex and a lipid membrane for encapsulating the complex therein. The lipid membrane may be either a lipid monolayer membrane (lipid monomolecular membrane) or a lipid bilayer membrane (lipid bimolecular membrane). Incidentally, the lipid membrane may contain Compound (I), Compound (II), a neutral lipid, and/or a polymer. In addition, the lipid nano particle may contain a cationic lipid other than Compound (I) in the complex, and/or the lipid membrane.

In addition, further examples of the lipid nano particles include lipid nano particles constituted of a complex between a cationic lipid other than Compound (I) and a nucleic acid, or a complex between a combination having a cationic lipid other than Compound (I) with a neutral lipid and/or a polymer and a nucleic acid, and a lipid membrane for encapsulating the complex, and the lipid membrane containing Compound (I) in the lipid membrane. Also this case, the lipid membrane may be either a lipid monolayer membrane (lipid monomolecular membrane) or a lipid bilayer membrane (lipid bimolecular membrane). In addition, the lipid nano particle may contain a cationic lipid other than Compound (I) in the complex, and/or the lipid membrane.

The lipid nano particles in the present invention are more preferably lipid nano particles containing a complex between Compound (I) and the nucleic acid, lipid nano particles containing a complex between Compounds (I) or a cationic lipid other than Compound (I) and the nucleic acid, and a lipid membrane for encapsulating the complexes therein, the lipid membrane containing Compound (I); still more preferably lipid nano particles containing a complex between Compound (I) and the nucleic acid, or lipid nano particles containing a complex between Compound (I) and the nucleic acid, and a lipid membrane for encapsulating the complexes therein, the lipid membrane containing Compound (I); and most preferably lipid nano particles containing a complex between Compound (I) and the nucleic acid, and a lipid membrane for encapsulating the complexes therein, the lipid membrane containing Compound (I). Incidentally, the lipid membrane may contain a neutral lipid, and/or a polymer. In addition, the lipid nano particle may contain a cationic lipid other than Compound (I) in the complex, and/or the lipid membrane.

Examples of a form of the complex in all of the present invention, include a complex between a nucleic acid and a membrane composed a lipid monolayer (reversed micelle), a complex between a nucleic acid and a liposome, and a complex between a nucleic acid and a micelle. Of these, a complex between a nucleic acid and a membrane composed of a lipid monolayer and a complex between a nucleic acid and a liposome are preferable.

Examples of the lipid nano particle constituted of the complex and a lipid bilayer membrane for encapsulating the complex therein include a liposome constituted of the complex and a lipid bilayer membrane for encapsulating the complex.

Incidentally, the lipid nano particle of the present invention may contain a nucleic acid etc., but can also contain compounds chemically similar to nucleic acids.

In the lipid nano particle in the present invention, each of Compound (I) may be used solely or in admixture of plural kinds thereof. In addition, in Compound (I), a cationic lipid other than Compound (I) may be mixed.

Examples of the cationic lipid other than Compound (I) include DOTMA, DOTAP, and the like as disclosed in JP-A-61-161246 (corresponding to U.S. Pat. No. 5,049, 386); N-[1-(2,3-dioleyloxypropyl)]-N,N-dimethyl-N-hydroxyethylammonium bromide (DORIE), 2,3-dioleyloxy-N-[2-(spermine carboxamido)ethyl]-N,N-dimethyl-1-propanaminium trifluoroacetate (DOSPA), and the like as disclosed in International Publication Nos. WO91/16024 and WO97/019675; DLinDMA and the like as disclosed in International Publication No. WO2005/121348; and DLin-K-DMA and the like as disclosed in International Publication No. WO2009/086558; and (3R,4R)-3,4-bis((Z)-Hexadec-9-enyloxy)-1-methylpyrrolidine, N-Methyl-N,N-bis(2-((Z)-octadec-6-enyloxy)ethyl)amine and the like as disclosed in International Publication No. WO2011/136368. The cationic lipid other than Compound (I) is preferably a cationic lipid having a tertiary amine site having two unsubstituted alkyl groups, or a quaternary ammonium site having three unsubstituted alkyl groups, such as DOTMA, DOTAP, DORIE, DOSPA, DLinDMA, and DLin-K-DMA; and more preferably a cationic lipid having the tertiary amine site. The unsubstituted alkyl group in each of the tertiary amine site and the quaternary ammonium site is more preferably a methyl group.

When Compound (I) are used in admixture of plural kinds thereof or with a cationic lipid other than Compound (I) in the lipid nano particle of the present invention, or the lipid nano particle of the present invention includes a lipid nano particle containing a complex between a cationic lipid other than Compound (I) and the nucleic acid, or a complex between a cationic lipid other than Compound (I) with the neutral lipid and/or a polymer and the nucleic acid, and a lipid bilayer membrane for encapsulating the complexes, and the lipid membrane containing Compound (I), it is more preferably that $X^3$ is absent, $Y^1$ is absent, $L^1$ is a single bond, and $R^3$ is alkyl having 1 to 6 carbon atoms in Compound (I).

The lipid nano particle in the present invention can be produced by a known production method or a method similar thereto and may be a lipid nano particle produced by any production method. For example, in the production of a liposome as one of lipid nano particles, a known preparation method of a liposome can be applied. Examples of the known preparation method of a liposome include a liposome preparation method by Bangham et al. (see *J. Mol. Biol.*, 1965, Vol. 13, pp. 238-252); an ethanol injection method (see *J. Cell Biol.*, 1975, Vol. 66, pp. 621-634); a French press method (see *FEBS Lett.*, 1979, Vol. 99, pp. 210-214); a freeze-thawing method (see *Arch. Biochem. Biophys.*, 1981, Vol. 212, pp. 186-194); a reverse phase evaporation method (see *Proc. Natl. Acad. Sci. USA*, 1978, Vol. 75, pp. 4194-4198); and a pH gradient method (see, for example, Japanese Patent Nos. 2572554 and 2659136, etc.) As a solution which disperses the liposome in the production of liposome, for example, water, an acid, an alkali, a variety of buffer solution, a saline, an amino acid infusion, and the like can be used. In addition, in the production of a liposome, it is also possible to add an antioxidant, for example, citric acid, ascorbic acid, cysteine, ethylenediaminetetraacetic acid (EDTA), etc., an isotonic agent, for example, glycerin, glucose, sodium chloride, etc., or the like. In addition, the liposome can also be produced by dissolving a lipid or the like in an organic solvent, for example, ethanol etc., distilling off the solvent, adding a saline or the like thereto, and stirring and shaking the mixture, thereby forming a liposome.

In addition, the lipid nano particle in the present invention can be produced by, for example, a method in which Compound (I), or mixture of Compound (I) and a cationic lipid other than Compound (I) are dissolved in chloroform in advance; subsequently, an aqueous solution of a nucleic acid and methanol are added thereto followed by mixing to form a cationic lipid/nucleic acid complex; furthermore, the chloroform layer is taken out, to which are then added a polyethylene glycolated phospholipid, a neutral lipid, and water to form a water-in-oil type (W/O) emulsion; and the emulsion is treated by a reverse phase evaporation method (see JP-T-2002-508765); a method in which a nucleic acid is dissolved in an acidic electrolyte aqueous solution, to which is then added a lipid (in ethanol); an ethanol concentration is decreased to 20 v/v %, thereby preparing lipid nano particle including the nucleic acid therein; the lipid nano particle is subjected to sizing filtration and dialysis to remove the excessive ethanol; and the resulting sample is further subjected to dialysis while increasing the pH, thereby removing the nucleic acid attached onto the lipid nano particle surface (see JP-T-2002-501511 and Biochimica et Biophysica Acta, 2001, Vol. 1510, pp. 152-166); and the like.

Among the lipid nano particles in the present invention, the liposome constituted of a complex between Compound (I) and the nucleic acid, or a complex between a combination having Compound (I) with a neutral lipid and/or a polymer and a nucleic acid and a lipid bilayer membrane having the complex encapsulated therein can be produced according to a production method described in, for example, International Publication Nos. WO02/28367 and WO2006/080118, etc.

In addition, among the lipid nano particles in the present invention, for example, the lipid nano particle constituted of a complex between Compound (I) and the nucleic acid, or a complex between a combination having Compound (I) with a neutral lipid and/or a polymer and a nucleic acid, and a lipid membrane for encapsulating the complex, the lipid membrane containing Compound (I) and/or a cationic lipid other than Compound (I); the lipid nano particle constituted of a complex between a cationic lipid other than Compound (I) and a nucleic acid, or a complex between a combination having a cationic lipid other than Compound (I) with a neutral lipid and/or a polymer and a nucleic acid, and a lipid membrane for encapsulating the complex, the lipid membrane containing Compound (I) or Compound (I) and a cationic lipid other than Compound (I); and the like can be obtained by producing the respective complexes in accordance with a production method described in International Publication Nos. WO02/28367 and WO2006/080118, etc., dispersing the complexes in water or an 0 to 20% ethanol aqueous solution without dissolving them (solution A), separately dissolving the respective lipid components in an ethanol aqueous solution (solution B), mixing the solution A and the solution B in equivalent amount, and further properly adding water thereto. Incidentally, As the cationic lipid in the solution A and B, Compound (I) and a cationic lipid other than Compound (I) may be used solely in kind or in admixture of plural kinds thereof.

Incidentally, in the present invention, those in which during the production and after the production of the lipid nano particle constituted of a complex between Compound (I) and the nucleic acid, or a complex between a combination having Compound (I) with a neutral lipid and/or a polymer and a nucleic acid, and a lipid membrane for encapsulating the complex, the lipid membrane containing Compound (I) and/or a cationic lipid other than Compound (I); the lipid nano particle constituted of a complex between a cationic lipid other than Compound (I) and a nucleic acid, or a complex between a combination having a cationic lipid other than Compound (I) with a neutral lipid and/or a polymer and a nucleic acid, and a lipid membrane for encapsulating the complex, the lipid membrane containing Compound (I); and the like, an electrostatic interaction between the nucleic acid in the complex and the cationic lipid in the lipid membrane, or fusion between the cationic lipid in the complex and the cationic lipid in the lipid membrane has caused displacement of the structures of the complex and the membrane are also included in the lipid nano particle constituted of a complex between Compound (I) and the nucleic acid, or a complex between a combination having Compound (I) with a neutral lipid and/or a polymer and a nucleic acid, and a lipid membrane for encapsulating the complex, the lipid membrane containing Compound (I) and/or a cationic lipid other than Compound (I); the lipid nano particle constituted of a complex between a cationic lipid other than Compound (I) and a nucleic acid, or a complex between a combination having a cationic lipid other than Compound (I) with a neutral lipid and/or a polymer and a nucleic acid, and a lipid membrane for encapsulating the complex, the lipid membrane containing Compound (I); and the like.

Among the lipid nano particles in the present invention, a total number of molecules of Compounds (I) in the complex is preferably 0.5 to 8 parts, more preferably 1.5 to 5 parts, further more preferably 2 to 3 parts relative to 1 part by a number of phosphorus atoms in the nucleic acid. Further, a total number of molecules of Compounds (I), and the cationic lipid other than Compounds (I) in the complex is preferably 0.5 to 8 parts, more preferably 1.5 to 5 parts, further more preferably 2 to 3 parts relative to 1 part by a number of phosphorus atoms in the nucleic acid.

In the case where the lipid nano particle of the present invention is constituted of the complex and the lipid membrane for encapsulating the complex therein, a total number of molecules of Compounds (I) in the lipid nano particle is preferably 1 to 15 parts, more preferably 2.5 to 10 parts, further more preferably 3.5 to 8 parts relative to 1 part by a number of phosphorus atoms in the nucleic acid. Further, a total number of molecules of Compounds (I), and the cationic lipid other than Compounds (I) in the lipid nano particle is preferably 1 to 15 parts, more preferably 2.5 to 10 parts, further more preferably 3.5 to 8 parts relative to 1 part by a number of phosphorus atoms in the nucleic acid.

A lipid nano particle containing a nucleic acid (having the same definition as described above), preferably the double-stranded nucleic acid, and any cationic lipid, preferably Compound (I) and/or a cationic lipid other than Compound (I), can be obtained by producing complexes between the nucleic acid and liposome comprising the cationic lipid in accordance with a production method described in International Publications Nos. WO/02/28367 and WO/2006/080118, etc., dispersing the complexes in water or an 0 to 20% ethanol aqueous solution without being dissolved (Solution A), separately dissolving the cationic lipid in a ethanol aqueous solution (Solution B), mixing Solution A and Solution B by the volume ratio 1:1 or in equivalent amount, and further properly adding water. Preferably, the lipid nano particle is a lipid nano particle containing a complex between the cationic lipid and the nucleic acid, and a lipid membrane for encapsulating the complexes therein. Further preferably, the lipid nano particle is a lipid nano particle containing a complex between a membrane composed of a lipid monolayer (reversed micelle) of the cationic lipid and the nucleic acid, and a lipid membrane for encapsulating the complexes therein. The lipid membrane may be either a lipid monolayer membrane (lipid monomolecular membrane) or a lipid bilayer membrane (lipid bimolecular membrane).

In addition, a liposome in the complexes between the nucleic acid and liposome is preferable to adjust the average particle diameter to a diameter shown below. The average particle diameter is preferably from about 10 nm to 400 nm, more preferably from about 30 nm to 110 nm, and still more preferably from about 40 nm to 80 nm. In addition, the lipid nano particle may contain a neutral lipid and/or a polymer in the lipid membrane. In addition, as long as Solution A can make the complex between liposome and the nucleic acid, the ethanol concentration may be 20 to 40%.

In addition, instead of mixing Solution A and Solution B in equivalent amount, it may replace with mixing Solution A and Solution B by a appropriately volume ratio which the complex does not dissolve and the cationic lipid in solution B does not dissolve after mixing Solution A and Solution B, preferably the ethanol concentration is 30 to 60%, or the complex does not dissolve after mixing Solution A and Solution B and the cationic lipid in solution B does not dissolve after mixing water and mixture of Solution A and Solution B.

The complexes between the nucleic acid and the liposome in Solution A are transformed to the complex between a membrane composed of a lipid monolayer (reversed micelle) of the cationic lipid and the nucleic acid after mixing of Solution A and Solution B, and further properly adding water. Preferably, the lipid nano particle obtained by the method is a lipid nano particle containing a complex between the cationic lipid and the nucleic acid, and a lipid membrane for encapsulating the complexes therein. Further preferably, the lipid nano particle is a lipid nano particle containing a complex between a membrane composed of a lipid monolayer (reversed micelle) of the cationic lipid and the nucleic acid, and a lipid membrane comprising the cationic lipid for encapsulating the complexes therein. The manufacturability (yield and/or homogeneity) is excellent.

A total number of molecules of the cationic lipid in the complexes in Solution A are preferably 0.5 to 8 parts, more preferably 1.5 to 5 parts, further more preferably 2 to 3 parts relative to 1 part by a number of phosphorus atoms in the nucleic acid.

In the case where the composition is a lipid nano particle containing a complex between a membrane composed of a lipid monolayer (reversed micelle) of the cationic lipid and the nucleic acid, and a lipid membrane for encapsulating the complexes therein, a total number of molecules of cationic lipid in the complex and membrane is preferably 1 to 15 parts, more preferably 2.5 to 10 parts, further more preferably 3.5 to 8 parts relative to 1 part by a number of phosphorus atoms in the nucleic acid.

The neutral lipid may be any lipid including a simple lipid, a complex lipid, and a derived lipid. Examples thereof include a phospholipid, a glyceroglycolipid, a sphingoglycolipid, a sphingoid, and a sterol. However, it should not be construed that the present invention is limited thereto.

In the case where the lipid nano particle of the present invention contains the neutral lipid, a total number of molecules of the neutral lipid is preferably 0.1 to 1.8 parts, more preferably 0.3 to 1.2 parts, further more preferably 0.4 to 0.9 parts relative to 1 part by a total number of molecules of Compound (I) and the cationic lipid other than Compound (I). The lipid nano particle either in the present invention may contain the neutral lipid in the complex, or in the lipid membrane for encapsulating the complex therein. It is more preferable that the neutral lipid is at least contained in the lipid membrane; and still more preferable that the neutral lipid is contained both in the complex and in the lipid membrane.

Examples of the phospholipid in the neutral lipid include natural or synthetic phospholipids such as phosphatidylcholines (specifically, soybean phosphatidylcholine, egg yolk phosphatidylcholine (EPC), distearoyl phosphatidylcholine (DSPC), dipalmitoyl phosphatidylcholine (DPPC), palmitoyloleoyl phosphatidylcholine (POPC), dimyristoyl phosphatidylcholine (DMPC), dioleoyl phosphatidylcholine (DOPC), etc.), phosphatidylethanolamines (specifically, distearoyl phosphatidylethanolamine (DSPE), dipalmitoyl phosphatidylethanolamine (DPPE), dioleoyl phosphatidylethanolamine (DOPE), dimyristoyl phosphoethanolamine (DMPE), 16-O-monomethyl PE, 16-O-dimethyl PE, 18-1-trans PE, palmitoyloleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyloleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphate, etc.), glycerophosphonolipids, sphingophosphonolipids, natural lecithins (specifically, egg yolk lecithin, soybean lecithin, etc.), and hydrogenated phospholipids (specifically, hydrogenated soybean phosphatidylcholine etc.)

Examples of the glyceroglycolipid in the neutral lipid include sulfoxyribosyl glyceride, diglycosyl diglyceride, digalactosyl diglyceride, galactosyl diglyceride, and glycosyl diglyceride.

Examples of the sphingoglycolipid in the neutral lipid include galactosyl cerebroside, lactosyl cerebroside, and ganglioside.

Examples of the sphingoid in the neutral lipid include sphingan, icosasphingan, sphingosine, and derivatives thereof. Examples of the derivative include those in which —NH$_2$ of sphingan, icosasphingan, sphingosine, or the like is replaced with —NHCO(CH$_2$)$_x$CH$_3$ (in the formula, x is an integer of from 0 to 18, with 6, 12, or 18 being preferable).

Examples of the sterol in the neutral lipid include cholesterol, dihydrocholesterol, lanosterol, β-sitosterol, campesterol, stigmasterol, brassicasterol, ergocasterol, fucosterol, and 3β-[N—(N',N'-dimethylaminoethyl)carbamoyl]cholesterol (DC-Chol).

The polymer may be one or more polymer micelles selected from, for example, protein, albumin, dextran, polyfect, chitosan, dextran sulfate; and polymers, for example, such as poly-L-lysine, polyethyleneimine, polyaspartic acid, a copolymer of styrene and maleic acid, a copolymer of isopropylacrylamide and acrylpyrrolidone, polyethylene glycol modified dendrimer, polylactic acid, polylactic acid polyglycolic acid, and polyethylene glycolated polylactic acid, and salt thereof.

Here, the salt of the polymer includes, for example, a metal salt, an ammonium salt, an acid addition salt, an organic amine addition salt, an amino acid addition salt, and the like. Examples of the metal salt include alkali metal salts such as a lithium salt, a sodium salt and a potassium salt; alkaline earth metal salts such as a magnesium salt and a calcium salt; an aluminum salt; a zinc salt, and the like. Examples of the ammonium salt include salts of ammonium, tetramethylammonium, or the like. Examples of the acid addition salt include inorganates such as a hydrochloride, a sulfate, a nitrate, and a phosphate, and organates such as an acetate, a maleate, a fumarate, and a citrate. Examples of the organic amine addition salt include addition salts of morpholine, piperidine, or the like, and examples of the amino acid addition salt include addition salts of glycine, phenylalanine, aspartic acid, glutamic acid, lysine, or the like.

In addition, the lipid nano particles of the present invention are preferred to comprise, for example, a lipid conjugate or a fatty acid conjugate of at least one substance selected from sugar, peptide, nucleic acid, and water-soluble polymer. The lipid nano particles may also comprise a surfactant or the like. A lipid conjugate or a fatty acid conjugate of at least one substance selected from sugar, peptide, nucleic acid, and water-soluble polymer, or a surfactant may be comprised in the complex, or may be comprised in the lipid membrane. It is more preferable that the lipid conjugate or a fatty acid conjugate of at least one substance selected from sugar, peptide, nucleic acid, and water-soluble polymer, or a surfactant is contained in the complex and the lipid membrane.

In the case where the lipid nano particles of the present invention contain the lipid conjugate or a fatty acid conjugate of at least one substance selected from sugar, peptide, nucleic acid, and water-soluble polymer, or a surfactant, a total number of molecules of the lipid conjugate or a fatty acid conjugate of at least one substance selected from sugar, peptide, nucleic acid, and water-soluble polymer, or a surfactant is preferably 0.05 to 0.3 parts, more preferably 0.07 to 0.25 parts, further more preferably 0.1 to 0.2 parts relative to 1 part by a total number of molecules of Compound (I) and the cationic lipid other than Compound (I).

The lipid conjugate or fatty acid conjugate of at least one substance selected from sugar, peptide, nucleic acid, and water-soluble polymer, or the surfactant is preferably a glycolipid, or a lipid conjugate or a fatty acid conjugate of a water-soluble polymer, more preferably a lipid conjugate or a fatty acid conjugate of a water-soluble polymer. Preferably, the lipid conjugate or fatty acid conjugate of at least one substance selected from sugar, peptide, nucleic acid, and water-soluble polymer, or the surfactant is a substance having dual properties in which a part of the molecule has the property to bind to the other constituent component(s) of the lipid nano particles through, for example, hydrophobic affinity, electrostatic interaction, and the like, whereas other parts of the molecule have the property to bind to the solvent used for the production of the lipid nano particles, through, for example, hydrophilic affinity, electrostatic interaction, and the like.

Examples of the lipid conjugate or fatty acid conjugate of sugar, peptide or nucleic acid include products formed by means of binding of sugars (such as sucrose, sorbitol, lactose, etc), peptides (such as casein-derived peptides, egg white-derived peptides, soybean-derived peptides, glutathione, etc) or nucleic acids (such as DNA, RNA, plasmids, siRNA ODN, etc) with the neutral lipids as exemplified above in the definition of the lipid nano particles or Compound (I), or with fatty acids (such as stearic acid, palmitic acid, myristic acid, lauric acid, etc).

Examples of the lipid conjugate or fatty acid conjugate of sugar include the glyceroglycolipids, the sphingoglycolipids, and the like as exemplified above in the definition of the lipid nano particles.

Examples of the lipid conjugate or fatty acid conjugate of a water-soluble polymer include products formed by means of binding of the neutral lipid as exemplified above in the definition of the lipid nano particle or Compound (I), or a fatty acid, for example, stearic acid, palmitic acid, myristic acid, lauric acid, etc. with, for example, polyethylene glycol, polyglycerin, polyethyleneimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or a derivative thereof, and salts thereof. More preferred examples thereof include lipid conjugates or fatty acid conjugates such as polyethylene glycol derivatives and polyglycerin derivatives. Still more preferred examples thereof include lipid conjugates or fatty acid conjugates of a polyethylene glycol derivative, and salts thereof.

Examples of the lipid conjugate or fatty acid conjugate of a polyethylene glycol derivative include polyethylene glycolated lipids (specifically, polyethylene glycol-phosphatidylethanolamines (more specifically, 1,2-distearoyl-sn-glycero-3-phosphoethanolamine-N-[methoxy(polyethylene glycol)-2000] (PEG-DSPE), 1,2-dimyristoyl-sn-glycero-3-phosphoethanolamine-N-[methoxy(polyethylene glycol)-2000] (PEG-DMPE), etc.), polyoxyethylene hydrogenated castor oil 60, CREMOPHOR EL, and the like), polyethylene glycol sorbitan fatty acid esters (specifically, polyoxyethylene sorbitan monooleate, etc.), and polyethylene glycol fatty acid esters; preferred examples thereof include polyethylene glycolated lipids.

Examples of the lipid conjugate or fatty acid conjugate of a polyglycerol derivative include polyglycerolated lipids (specifically, polyglycerol phosphatidyl ethanolamine and the like), polyglycerol fatty acid esters and the like, and more preferred examples thereof include polyglycerolated lipids.

Examples of the surfactant include polyoxyethylene sorbitan monooleates (specifically, Polysorbate 80, and the like), polyoxyethylene polyoxypropylene glycols (specifically, Pluronic F68, and the like), sorbitan fatty acid esters (specifically, sorbitan monolaurate, sorbitan monooleate, and the like), polyoxyethylene derivatives (specifically, polyoxyethylene hydrogenated castor oil 60, polyoxyethylene lauryl alcohol, and the like), glycerin fatty acid esters, and polyethylene glycolalkyl ethers. Preferred examples thereof include polyoxyethylene polyoxypropylene glycols, glycerin fatty acid esters, polyethylene glycolalkyl ethers, and the like.

In addition, in the lipid nano particle in the present invention, surface modification of the lipid nano particle with, for example, a polymer, a polyoxyethylene derivative, etc. can be arbitrarily carried out [see ed. D. D. Lasic, F. Martin, *Stealth Liposomes*, CRC Press Inc., US, 1995, p. 93-102]. Examples of the polymer which can be used for the surface modification include dextran, pullulan, mannan, amylopectin, and hydroxyethyl starch. Examples of the polyoxyethylene derivative include polysorbate 80, Pluronic F68, polyoxyethylene hydrogenated castor oil 60, polyoxyethylene lauryl alcohol, and PEG-DSPE. The lipid conjugate or a fatty acid conjugate of at least one substance selected from sugar, peptide, nucleic acid, and water-soluble polymer, or a surfactant can be contained in the lipid nano particle or the complex and the lipid membrane in the lipid nano particle by means of the surface modification of the lipid nano particle.

In addition, it can perform arbitrarily also making it bind directly with the surface of the lipid nanoparticle of the present invention by carrying out the covalent bond of the targeting ligand to the polar head residue of the lipid component of the lipid nano particle of the present invention. (see International Publication No. WO2006/116107)

An average particle diameter of the lipid nano particle in present invention can be freely selected upon demand. It is preferable to adjust the average particle diameter to a diameter shown below. Examples of a method of adjusting the average particle diameter include an extrusion method, a method in which a large multilamellar liposome vesicle (MLV) and the like is mechanically pulverized (specifically using Manton-gaulin, a microfluidizer or the like) (see "Emulsion and Nanosuspensions for the Formulation of Poorly Soluble Drugs", edited by R. H. Muller, S. Benita and B. Bohm, Scientific Publishers, Stuttgart, Germany, pp. 267-294, 1998) and the like.

As for the size of the lipid nano particle in the present invention, an average particle diameter is preferably from about 10 nm to 1,000 nm, more preferably from about 30 nm to 300 nm, and still more preferably from about 50 nm to 200 nm.

By administering the lipid nano particle of the present invention to a mammalian cell, the nucleic acid in the lipid nano particle of the present invention can be introduced into the cell.

A method for administering the lipid nano particle of the present invention to a mammalian cell in vivo may be carried out according to the procedures of known transfection that can be performed in vivo. For example, by the intravenous administration of the lipid nano particle of the present invention to mammals including humans, the lipid nano particle is delivered to, for example, an organ or a site involving cancer or inflammation, and the nucleic acid in the lipid nano particle of the present invention can be introduced into the cells at these organs or sites. The organs or sites involving cancer or inflammation are not particularly limited. Examples thereof include stomach, large intestine, liver, lungs, spleen, pancreas, kidneys, bladder, skin, blood vessel, and eye ball. In addition, by the intravenous administration of the lipid nano particle of the present invention to mammals including humans, the lipid nano particle can be delivered to, for example, blood vessel, liver, lungs, spleen, and/or kidneys, and the nucleic acid in the composition of the present invention can be introduced into the cells at these organs or sites. The liver, lung, spleen, and/or kidney cells may be any of normal cells, cells associated with cancer or inflammation, and cells associated with other diseases.

When the nucleic acid in the lipid nano particle in the present invention is a nucleic acid having an activity of suppressing the expression of the target gene by utilizing RNA interference (RNAi), RNA that suppress the expression of the gene can be introduced to mammalian cells in vivo, and expression of genes can be suppressed. The administration target is preferably human.

In addition, when the target gene of lipid nano particle in the present invention is, for example, a gene associated with tumor or inflammation, the lipid nano particle of the present invention can be used as a therapeutic agent or a preventive agent for cancer or inflammatory disease, preferably a therapeutic agent or a preventive agent for solid cancer or for inflammation in blood vessels or in the vicinity of blood vessels. Specifically, when the target gene of the lipid nano particle of the present invention is, for example, a gene associated with angiogenesis, the lipid nano particle of the present invention can suppress the proliferation, angiogenesis, or the like in the vascular smooth muscle, and can thus be used as a therapeutic agent or a preventive agent for cancer or inflammatory disease that involves, for example, proliferation or angiogenesis in the vascular smooth muscle. When Compound (I) are used in admixture of plural kinds thereof or with a cationic lipid other than Compound (I), it is possible to decrease the amount of consumption compared to when used alone cationic lipids individual. Thus, it is possible to reduce the extent and incidence of undesirable events related the cationic lipids.

Specifically, the present invention also provides a cancer or inflammatory disease therapeutic method that includes administering the lipid nano particles of the present invention to a mammal. The administration target is preferably human, more preferably humans having cancer or inflammatory disease.

Further, the lipid nano particles of the present invention also can be used as a tool for verifing the effectiveness of suppression of target gene in an in vivo efficacy evaluation model concerning the cancer or inflammatory disease therapeutic or preventive agent.

The lipid nano particle of the present invention also can be used as a preparation for, for example, stabilizing the nucleic acid in biogenic substances (for example, blood, digestive tract, and the like) such as blood components, reducing side effects, or increasing drug accumulation in tissues or organs containing the expression site of the target gene.

When the lipid nano particle of the present invention is used as a medicament, specifically a therapeutic agent or preventive agent for cancer, inflammatory disease, or the like, it is desirable to use an administration route that is most effective for the treatment. The administration route may be parenteral or oral, including buccal administration, airway administration, rectal administration, subcutaneous administration, intramuscular administration, intravenous administration, and the like. Intravenous administration and intramuscular administration are preferable, and intravenous administration is more preferable.

The dose may vary depending upon factors such as the conditions and the age of a subject, and the administration route. For example, the administration may be made in a daily dose of, for example, about 0.1 fig to 1,000 mg in terms of the nucleic acid.

As a preparation suitable for the intravenous administration or intramuscular administration, for example, an injection can be exemplified, and it is also possible to use a dispersion liquid of the lipid nano particle prepared by the foregoing method as it is in the form of, for example, an injection or the like. However, the dispersion liquid can also be used after removing the solvent from the dispersion liquid by, for example, filtration, centrifugation, or the like, or after lyophilizing it or the dispersion liquid supplemented with an excipient such as mannitol, lactose, trehalose, maltose, or glycine.

In the case of an injection, it is preferable that an injection is prepared by mixing, for example, water, an acid, an alkali, a variety of buffer solution, a saline, an amino acid infusion, or the like with the foregoing dispersion liquid of the lipid nano particle or the foregoing lipid nano particle obtained by removing the solvent or lyophilization. In addition, it is also possible to prepare an injection by adding an antioxidant such as citric acid, ascorbic acid, cysteine, or EDTA, an isotonic agent such as glycerin, glucose, or sodium chloride, or the like thereto. In addition, it can also be cryopreserved by adding a cryopreservation agent such as glycerin thereto.

Next, the present invention is specifically described with reference to the following Examples and Test Examples. However, it should not be construed that the present invention is limited to these Examples and Test Examples.

Incidentally, proton nuclear magnetic resonance spectra ($^1$H NMR) shown in Referential Examples are those measured at 270 MHz, 300 MHz, or 400 MHz, and there may be the case where an exchangeable proton is not distinctly observed depending upon the compound and measuring conditions. Incidentally, regarding the expression for multiplicity of a signal is a usually used expression is used. The term "br" indicates an apparently broad signal.

REFERENTIAL EXAMPLE 1

Methyl di((9Z,12Z)-octadeca-9,12-dienyl)amine (Compound 1)

To methylamine (manufactured by Aldrich, about 2 mol/L tetrahydrofuran solution, 10.5 mL, 21.0 mmol), (9Z,12Z)-octadeca-9,12-dienyl methanesulfonate (manufactured by Nu-Chek Prep, Inc., 1.03 g, 3.00 mmol) was added, and the contents were heated with stirring at 150° C. for 90 minutes by using a microwave reaction apparatus. The reaction solution was diluted with ethyl acetate, washed successively with a 2 mol/L sodium hydroxide aqueous solution and saturated salt water, and dried over anhydrous magnesium sulfate. Thereafter, the resultant was filtered and concentrated under reduced pressure to obtain a crude product of methyl((9Z,12Z)-octadeca-9,12-dienyl)amine.

To the obtained crude product, (9Z,12Z)-octadeca-9,12-dienyl methanesulfonate (manufactured by Nu-Chek Prep, Inc., 0.93 g, 2.70 mmol) and a 50% sodium hydroxide aqueous solution (0.960 g, 12.0 mmol) were added, and the contents were heated with stirring at 135° C. for 60 minutes on an oil bath. After cooling to room temperature, the reaction solution was diluted with ethyl acetate, washed successively with water and saturated salt water, and dried over anhydrous magnesium sulfate. Thereafter, the resultant was filtered and concentrated under reduced pressure. The obtained residue was purified by means of silica gel column chromatography (chloroform/methanol: 100/0 to 97/3), thereby obtaining Compound 1 (1.07 g, 67.2%).

ESI-MS m/z: 529 (M+H)$^+$; $^1$H-NMR (CDCl$_3$) δ: 0.89 (t, J=6.7 Hz, 6H), 1.29 (br s, 32H), 1.40 to 1.51 (m, 4H), 1.97 to 2.06 (m, 8H), 2.20 (s, 3H), 2.30 (t, J=7.6 Hz, 4H), 2.77 (t, J=5.8 Hz, 4H), 5.28 to 5.43 (m, 8H)

REFERENTIAL EXAMPLE 2

Methyl di((Z)-hexadec-9-enyl)amine (Compound 2)

Compound 2 (0.491 g, 51.6%) was obtained in the same manner as that in Referential Example 1, by using methylamine (manufactured by Aldrich, about 2 mol/L tetrahydrofuran solution, 10.0 mL, 20.0 mmol) and (Z)-hexadec-9-enyl methanesulfonate (manufactured by Nu-Chek Prep, Inc., 1.21 g, 3.80 mmol).

ESI-MS m/z: 477 (M+H)$^+$; $^1$H-NMR (CDCl$_3$) δ: 0.88 (t, J=6.7 Hz, 6H), 1.29 (br s, 36H), 1.46 to 1.57 (m, 4H), 1.97 to 2.05 (m, 8H), 2.33 (s, 3H), 2.45 (t, J=7.9 Hz, 4H), 5.29 to 5.41 (m, 4H)

REFERENTIAL EXAMPLE 3

Methyl di((11Z,14Z)-icosa-11,14-dienyl)amine (Compound 3)

Compound 3 (1.27 g, 54.4%) was obtained in the same manner as that in Referential Example 1, by using methylamine (manufactured by Aldrich, about 2 mol/L tetrahydrofuran solution, 16.0 mL, 32.0 mmol) and (11Z,14Z)-icosa-11,14-dienyl methanesulfonate (manufactured by Nu-Chek Prep, Inc., 2.98 g, 8.00 mmol).

ESI-MS m/z: 585 (M+H)$^+$; $^1$H-NMR (CDCl$_3$) δ: 0.89 (t, J=6.7 Hz, 6H), 1.27 (br s, 40H), 1.39 to 1.51 (m, 4H), 2.01 to 2.09 (m, 8H), 2.20 (s, 3H), 2.30 (t, J=7.6 Hz, 4H), 2.79 (d, J=6.3 Hz, 4H), 5.28 to 5.43 (m, 8H)

REFERENTIAL EXAMPLE 4

Di((9Z,12Z)-octadeca-9,12-dienyl)amine (Compound 4)

Compound 4 (0.838 g, 36.2%) was obtained in the same manner as that in Referential Example 1, by using ammonia (manufactured by Tokyo Chemical Industry Co., Ltd., about 2 mol/L methanol solution, 18.0 mL, 36.0 mmol) and (9Z,12Z)-octadeca-9,12-dienyl methanesulfonate (manufactured by Nu-Chek Prep, Inc., 2.79 g, 8.10 mmol).

ESI-MS m/z: 515 (M+H)$^+$; $^1$H-NMR (CDCl$_3$) δ: 0.89 (t, J=6.9 Hz, 6H), 1.30 (br s, 33H), 1.41 to 1.54 (m, 4H), 2.01 to 2.09 (m, 8H), 2.59 (t, J=7.2 Hz, 4H), 2.77 (d, J=5.6 Hz, 4H), 5.28 to 5.43 (m, 8H)

REFERENTIAL EXAMPLE 5

Di((Z)-octadec-9-enyl)amine (Compound 5)

Compound 5 (0.562 g, 36.2%) was obtained in the same manner as that in Referential Example 1, by using ammonia (manufactured by Tokyo Chemical Industry Co., Ltd., about 2 mol/L methanol solution, 12.0 mL, 24.0 mmol) and (Z)-octadec-9-enyl methanesulfonate (manufactured by Nu-Chek Prep, Inc., 1.87 g, 5.40 mmol).

ESI-MS m/z: 519 (M+H)$^+$; $^1$H-NMR (CDCl$_3$) δ: 0.88 (t, J=6.7 Hz, 6H), 1.29 (br s, 45H), 1.41 to 1.52 (m, 4H), 1.97 to 2.05 (m, 8H), 2.58 (t, J=7.2 Hz, 4H), 5.28 to 5.40 (m, 4H)

REFERENTIAL EXAMPLE 6

Methyl di((Z)-octadec-9-enyl)amine (Compound 6)

Compound 6 (1.20 g, 70.2%) was obtained in the same manner as that in Referential Example 1, by using methylamine (manufactured by Aldrich, about 2 mol/L tetrahydrofuran solution, 11.2 mL, 22.4 mmol) and (Z)-octadec-9-enyl methanesulfonate (manufactured by Nu-Chek Prep, Inc., 2.11 g, 6.09 mmol).

ESI-MS m/z: 533 (M+H)$^+$; $^1$H-NMR (CDCl$_3$) δ: 0.88 (t, J=6.6 Hz, 6H), 1.27 (br s, 44H), 1.39 to 1.50 (m, 4H), 1.97 to 2.06 (m, 8H), 2.20 (s, 3H), 2.30 (t, J=7.6 Hz, 4H), 5.28 to 5.40 (m, 4H)

EXAMPLE 1

Preparations were produced using Compound 1 obtained in Referential Example 1, as follows.

APO-B siRNA was used as the nucleic acid. APO-B siRNA suppresses expression of an apolipoprotein-B (hereinafter, "apo-b") gene and has a sense strand with the base sequence 5'-GmUCAmUCACACmUGAAmUACCAAmU-3' (SEQ ID NO:1) (the sugars attached to the bases appended with m are 2'-O-methyl-substituted riboses), and an antisense strand with the base sequence 5'-AUUGGUAUUCAGU-GUGAUGACAC-3' (SEQ ID NO:2) (the 5'-end is phosphorylated). The sense strand and the antisense strand were obtained from Nippon EGT, GeneDesign, Inc., Invitrogen or Hokkaido System Science Co., Ltd., and annealed to prepare the nucleic acid (hereinafter, "apo-b siRNA").

A solution comprising the constituent components was prepared by dissolving each of the weighed samples in 90 vol % ethanol in 8.947/1.059/5.708/13.697 mmol/L [Compound 1/sodium 1,2-dimyristoyl-sn-glycero-3-phosphoethanolamine-N-(methoxy(polyethylene glycol)-2000) (PEG-DMPE Na, (carbonylmethoxypolyethylene glycol 2000)-1,2-dimyristoyl-sn-glycero-3-phosphoethanolamine sodium salt, NOF Corporation)/distearoylphosphatidyl choline (DSPC, 1,2-distearoyl-sn-glycero-3-phosphocholine, NOF Corporation)/cholesterol (Avanti Polar Lipids)]. Separately, apo-b siRNA/distilled water (24 mg/mL) was diluted with a Tris-EDTA buffer (200 mM Tris-HCl, 20 mM EDTA, Invitrogen) and a 20 mM citric acid buffer (pH 5.0) to prepare a 1.5 mg/mL apo-b siRNA aqueous solution (2 mM Tris-EDTA/20 mM citric acid buffer, pH 5.0).

The resulting lipid solution was heated to 37° C., and a 100-μL portion was transferred to a preparation container. The apo-b siRNA aqueous solution (100 μL) was then added thereto while being stirred. Then, a 20 mM citric acid buffer (containing 300 mM NaCl, pH 6.0; 200 μL) was added to the lipid nucleic acid mixed suspension (200 μL) while being stirred. The siRNA concentration was brought to 10 μM by dropping a Dulbecco phosphate buffer (DPBS, Invitrogen; 662 μL), and preparations (lipid nano particles) comprising Compound 1 and the nucleic acid) were obtained.

An average particle diameter of lipid nano particles in the preparation measured using a particle size analyzer (Malvern; Zetasizer Nano ZS) was 155.9 nm.

EXAMPLE 2

A preparation was obtained in the same manner as that in Example 1, except that Compound 1 was changed to Compound 2. The average particle diameter of lipid nano particles in the preparation was 122.7 nm.

EXAMPLE 3

A preparation was obtained in the same manner as that in Example 1, except that Compound 1 was changed to Compound 3. The average particle diameter of lipid nano particles in the preparation was 129.8 nm.

EXAMPLE 4

A preparation was obtained in the same manner as that in Example 1, except that Compound 1 was changed to Compound 4. The average particle diameter of lipid nano particles in the preparation was 139.5 nm.

EXAMPLE 5

A preparation was obtained in the same manner as that in Example 1, except that Compound 1 was changed to Compound 5.

The obtained preparation was concentrated using Amicon Ultra (manufactured by Millipore Corporation), further replaced with DPBS, and then filtered with a 0.2-μm filter (manufactured by Toyo Roshi Kaisha, Ltd.) within a clean bench. Furthermore, an siRNA concentration of the obtained preparation was measured, and the preparation was diluted with DPBS such that the siRNA concentration was 1.0 mg/mL. The average particle diameter of lipid nano particles in the preparation was 139.5 nm.

COMPARATIVE EXAMPLE 1

A preparation was obtained in the same manner as that in Example 1, except that Compound 1 was changed to DOTAP (compound A-1, Avanti Polar Lipids). The average particle diameter of lipid nano particles in the preparation was 104.0 nm.

COMPARATIVE EXAMPLE 2

A preparation was obtained in the same manner as that in Example 118, except that compound 1 was changed to DLinDMA (Compound A-2). The Compound A-2 was produced by a method described in WO2005/121348. The average particle diameter of lipid nano particles in the preparation was 131.6 nm.

The structures of Compound A-1 and A-2 used in Comparative Examples are shown in Tables 2.

TABLE 2

| Compound | Structure |
|---|---|
| A-1 | (structure: dioleoyl glycerol trimethylammonium chloride) |
| A-2 | (structure: dilinoleyl glyceryl dimethylaminoethyl ether) |

TEST EXAMPLE 1

The preparations obtained in Examples 1 to 4 (lipid nano particles comprising compounds 1 to 4 and the nucleic acid), and the preparations obtained in Comparative Examples 1 and 2 were introduced into human liver cancer-derived cell line HepG2 (HB-8065) by using the following method.

Each preparation diluted with Opti-MEM (GIBCO; 31985) to make the nucleic acid final concentrations 3 to 100 nM or 1 to 30 nM was dispensed in a 96-well culture plate in 20-μL portions. Then, HepG2 cells suspended in MEM containing 1.25% fetal bovine serum (FBS; SAFC Biosciences; 12203C) were inoculated in 6250 cells/80 μL/well, and cultured under 37° C., 5% $CO_2$ conditions to introduce the preparation into the HepG2 cells. Untreated cells were also inoculated as a negative control group.

The cells after the introduction of the preparation were cultured in a 37° C., 5% $CO_2$ incubator for 24 hours, and washed with ice-cooled phosphate buffered saline (PBS; GIBCO; 14190). Total RNA was collected, and cDNA was produced by reverse transcription reaction using the total RNA as a template, using a Cells-to-Ct Kit (Applied Bioscience; ABI; AM1728) according to the protocol attached to the kit.

By using the cDNA as a template, a PCR reaction was performed for the apo-b gene and the constitutively expressed gene D-glyceraldehyde-3-phosphate dehydrogenase (hereinafter, "gapdh") gene using a universal probe library (Roche Applied Science; 04683633001) as the probe. For the PCR, ABI7900HT Fast (ABI) was used according to the protocol attached to the system. The mRNA amplification amounts were measured, and a quasi-quantitative value for the apo-b mRNA was calculated using the gapdh mRNA amplification amount as the internal control. The apo-b mRNA level and the gapdh mRNA amplification amount in the negative control group were also measured in the same manner, and a quasi-quantitative value for the apo-b mRNA was calculated using the gapdh mRNA amplification amount as the internal control.

The apo-b mRNA expression rate was determined from the calculated apo-b mRNA quasi-quantitative value relative to the apo-b mRNA quasi-quantitative value of the negative control as 1. The results are presented in FIG. 1. The vertical axis represents the target gene mRNA expression rate relative to the negative control taken at 1. The horizontal axis represents nucleic acid concentration (nM), and the compound numbers and example numbers of the cationic lipids used.

As is clear FIG. 1, the apo-b gene mRNA expression rate after the introduction of the preparations obtained in Examples 1 to 4 (lipid nano particles comprising compounds 1 to 4 and the nucleic acid) into the human liver cancer-derived cell line HepG2 were weak suppressed as compared with the preparations obtained in Comparative Example 2.

TEST EXAMPLE 2

The preparations obtained in the same as Example 1-4 and the preparations obtained Example 5 (preparations using compounds 1 to 5), and the preparations obtained in Comparative Examples 1 and 2 (preparations using compounds A-1 and A-2) were subjected to an in vivo efficacy evaluation test in the following manner. Incidentally, each the preparations were condensed using the Amicon ultra (manufactured by Millipore Corporation) and collected after replacing a solvent by DPBS. The siRNA concentrations of the obtained preparations were quantified, and it were diluted to compensate for the examination.

After acclimatation breeding, each of the preparations is intravenously administered in a dose of 3 or 0.3 mg/kg of siRNA to mice. The blood was collected 48 hours after administration and was centrifuged at 3000 rpm, 20 min., and 4° C. using small cooled centrifuges (05PR-22: made by Hitachi, Ltd.). As the cholesterol count in the obtained serum, by using Cholesterol Assay Kit (the product made by Cayman Chemical, Cat#: 10007640), in accordance with the method written in the description of the product, the degree of fluorescence in a reference solution and a serum sample was measured by ARVO (530 nm/595 nm) or EnVision (531 nm/595 nm). The cholesterol concentration in serum was calculated with analytical curve prepared from the obtained degree of fluorescence.

Figure 2:
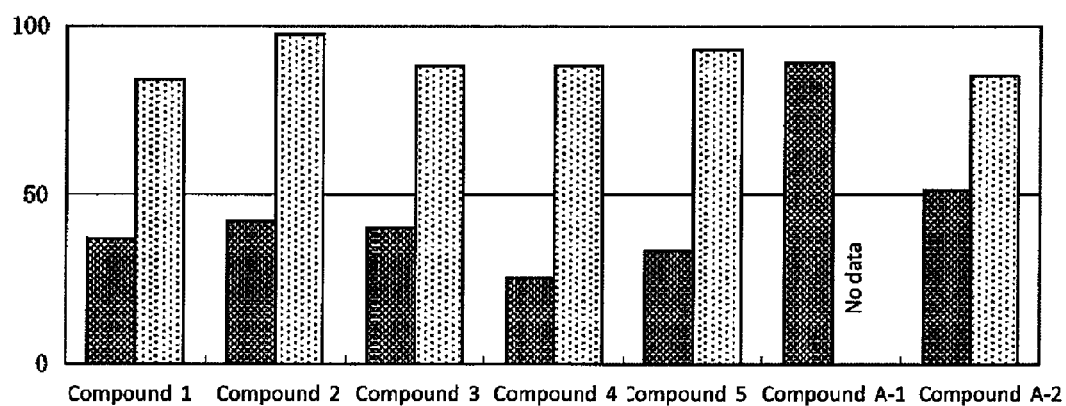
FIG. 2 shows an amount of cholesterol in blood 48 hours after the administration of the preparations obtained in the same as Example 1-4 and the preparations obtained Example 5 (preparations using compounds 1 to 5), and the preparations obtained in Comparative Examples 1 and 2 (preparations using compounds A-1 and A-2) to mice in an amount equivalent to 3 or 0.3 mg/kg CKAP5 siRNA. The ordinate represents a relative value of an amount of cholesterol while defining that of a saline-administered group as 100; the left bar and the right bar of each data represent 3 and 0.3 mg/kg CKAP5 siRNA-administered groups, respectively.

FIG. 2 shows an amount of cholesterol in blood. The ordinate represents a relative value of an amount of cholesterol while defining that of a saline-administered group as 100; the abscissa represents the compound numbers of the cationic lipids used.

As is clear from FIG. 2, the results of the in vivo efficacy evaluation test revealed that the preparations obtained in Examples 1 to 5 (lipid nano particles containing Compounds 1 to 5 and APO-B siRNA suppresses expression of apo-b gene) had stronger inhibition in the results of measurement of cholesterol concentration as the in vitro evaluation test than each preparations obtained by Comparative Examples 1 and 2. The results of the in vivo efficacy evaluation test revealed that the preparations in the present inventions had unexpectedly strong activity, although the preparations had weak transfection-activity in the results of the in vitro evaluation test (Test Example 1). It is found that the lipid nano particles are an outstanding lipid nanoparticle which carries out drug delivery satisfactorily into a cell in vivo. The effect is not expected by a person skilled in the art.

Therefore, it is found that the lipid nano particles of the present invention can be used to introduce nucleic acid into cell, and that Compound (I) is a cationic lipid which makes it easy to carry out drug delivery satisfactorily into a cell in vivo.

EXAMPLE 6

A preparation was produced in the following manner by using Compound 1 obtained in Referential Example 1.

CKAP5 siRNA was used as the nucleic acid. CKAP5 siRNA suppresses expression of CKAP5 gene and has a sense strand with the base sequence 5'-mGmGAAGCUG-GCGAUUAUGCAGAUUmUmA-3' (SEQ ID NO:3) (the sugars attached to the bases appended with m are 2'-0-methyl-substituted riboses), and an antisense strand with the base sequence 5'-UAAAUCUGCAUAAUCGCCAGC-UUCC-3' (SEQ ID NO:4) (the 5'-end is phosphorylated). The annealed sense strand and the antisense strand was obtained from Nippon EGT, GeneDesign, Inc., Invitrogen or Hokkaido System Science Co., Ltd., and was used after being dissolved in distilled water so as to have a concentration of 24 mg/mL (hereinafter referred to as "CKAP5 siRNA solution").

Compounds 1 and sodium 1,2-dimyristoyl-sn-glycero-3-phosphoethanolamine-N-(methoxy(polyethylene glycol)-2000) (PEG-DMPE Na, N-(carbonylmethoxypolyethylene glycol 2000)-1,2-dimyristoyl-sn-glycero-3-phosphoethanolamine sodium salt, manufactured by NOF Corporation) was suspended in a proportion of 57.3/5.52 mmol/L in an aqueous solution containing hydrochloric acid and ethanol, and stirring with a vortex mixer and heating was repeated, thereby obtaining a homogenous suspension. This suspension was allowed to pass through a 0.2-μm polycarbonate membrane filter and a 0.05-μm polycarbonate membrane filter at room temperature, thereby obtaining a dispersion liquid of lead particles. An average particle diameter of the lead particles obtained was measured by means of a dynamic light scattering (DLS) particle size analyzer and confirmed to fall within the range of from 30 nm to 100 nm. The CKAP5 siRNA solution was mixed with the obtained dispersion liquid of lead particles in a proportion of 3/1, to which was then added distilled water in an amount of three times, and the contents were mixed to prepare a dispersion liquid of cationic lipid/nucleic acid complex particles.

On the other hand, each lipid was weighed in a proportion of Compound 1 to sodium 1,2-distearoyl-sn-glycero-3-phosphoethanolamine-N-(methoxy(polyethylene glycol)-2000) (PEG-DSPE Na, N-(carbonylmethoxy polyethylene glycol 2000)-1,2-distearoyl-sn-glycro-3-phosphoethanolamine sodium salt, manufactured by NOF Corporation) to distearoyl phosphatidylcholine (DSPC, 1,2-distearoyl-sn-glycero-3-phosphocholine, manufactured by NOF Corporation) to cholesterol (manufactured by NOF Corporation) of 8.947/2.94/5.71/11.8 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/nucleic acid complex particle in a proportion of 1/1. The mixture was further mixed with distilled water in an amount of several times, thereby obtaining a crude preparation.

The obtained crude preparation was concentrated using Amicon Ultra (manufactured by Millipore Corporation), further replaced with a saline, and then filtered with a 0.2-μm filter (manufactured by Toyo Roshi Kaisha, Ltd.) within a clean bench. Furthermore, an siRNA concentration of the obtained preparation was measured, and the preparation was diluted with a saline such that the siRNA concentration was 1.0 mg/mL. An average particle diameter of lipid nano particles in the preparation was 86.0 nm.

EXAMPLE 7

A preparation was obtained in the same manner as that in Example 6, except that Compound 1 was changed to Compound 2. The average particle diameter of lipid nano particles in the preparation was 77.1 nm.

EXAMPLE 8

A preparation was obtained in the same manner as that in Example 6, except that Compound 1 was changed to Compound 6. The average particle diameter of lipid nano particles in the preparation was 81.5 nm.

EXAMPLE 9

A preparation was produced in the following manner by using Compound 1 obtained in Referential Example 1.

A dispersion liquid of cationic lipid/nucleic acid complex particles contained CKAP5 siRNA and lead particles are obtained in the same manner as that in Example 6.

On the other hand, each lipid was weighed in a proportion of Compound 1 and Trans-1-methyl-3,4-bis(((9Z,12Z)-octadeca-9,12-dienoyloxy)methyl)pyrrolidine (The Compound was produced by a method described in WO2011/136368) to sodium 1,2-distearoyl-sn-glycero-3-phosphoethanolamine-N-(methoxy(polyethylene glycol)-2000) (PEG-DSPE Na, N-(carbonylmethoxy polyethylene glycol 2000)-1,2-distearoyl-sn-glycro-3-phosphoethanolamine sodium salt, manufactured by NOF Corporation) to distearoyl phosphatidylcholine (DSPC, 1,2-distearoyl-sn-glycero-3-phosphocholine, manufactured by NOF Corporation) to cholesterol (manufactured by NOF Corporation) of 2.982/5.965/2.943/5.707/11.83 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/nucleic acid complex particle in a proportion of 1/1. The mixture was further mixed with distilled water in an amount of several times, thereby obtaining a crude preparation.

The obtained crude preparation was concentrated using Amicon Ultra (manufactured by Millipore Corporation), further replaced with a saline, and then filtered with a 0.2-μm filter (manufactured by Toyo Roshi Kaisha, Ltd.) within a clean bench. Furthermore, an siRNA concentration of the obtained preparation was measured, and the preparation was diluted with a saline such that the siRNA concentration was 1.0 mg/mL. An average particle diameter of lipid nano particles in the preparation was 93.9 nm.

TEST EXAMPLE 3

The preparations obtained in Examples 6 to 9 (lipid nano particles comprising Compound (I) and nucleic acid) were subjected to an in vivo mRNA knockdown evaluation test in the following manner.

MIA PaCa-2 that was a cell line derived from human pancreas cancer is received from the JCRB Cell Bank and cultivated with high glucose-containing DMEM (manufactured by GIBCO, 11995-073) containing a 10% inactivated fetal calf serum (manufactured by GIBCO) and 1 vol % penicillin-streptomycin (manufactured by GIBCO, 26253-84) under conditions at 37° C. and 5% $CO_2$. MIA PaCa-2 was suspended in PBS in a concentration of $1\times10^8$ cells/mL, and 100 µL of this cell suspension was transplanted into a dorsal subcutis of SCID mouse (delivered from NIPPON KUREA) ($1\times10^7$ cells/0.1 mL PBS/head). Six days after the transplantation, the mice were divided into groups consisting of three heads per group while taking the tumor volume as an index, and each of the preparations in Example 6 and 7 is intravenously administered in a dose of 10 mg/kg (10 mL/kg). As a saline-administered group, a saline was administered in a dose of 10 mL/kg. Before the administration and 48 hours after the administration, the weight of the mouse was measured. After the weight measurement, the mouse is euthanized, and the subcutaneous tumor is removed. The removed tumor was immediately frozen by liquid nitrogen and stored at -80° C. until it is used.

With respect to the obtained tumor sample, 1 mL of a Trizol reagent (manufactured by Invitrogen, 15596-018) and zirconia beads of 5 mm were added to a 2-mL round bottom tube containing the sample charged therein, and the contents were pulverized by Tissue lyser II (manufactured by QIAGEN) under conditions of ½s freq, 1.5 minutes×2 times. After the pulverization, centrifugation (at 10,000 rpm for 10 minutes) were conducted, the supernatant was recovered, to which was then added 200 µL of chloroform, and the contents were vigorously stirred, followed by again conducting centrifugation (at 15,000 rpm for 15 min). 200 µL of the obtained supernatant was extracted RNA using a automated nucleic acid extractor MagNA PURE (Roche) and Cellular RNA Large Volume Kit (Roche, 5467535). A concentration of the extracted RNA was measured by a trace absorption photometer Dropsense96 (Trinean), and RNA corresponding to from 200 to 1,000 ng was subjected to reverse transfer with a Transcriptor (manufactured by Roche, 4897030). The reaction solution and the reaction condition followed those described in the appended papers. The obtained cDNA sample is diluted ten times with $dH_2O$ and used as a template of qPCR. For the qPCR reaction, TaqMan Gene Expression Master Mix (manufactured by Applied Biosystems, 4369542) and TaqMan Gene Expression Assays (manufactured by Applied Biosystems, 4331182) were used. The conditions of the PCR reaction follows those described in the instruction manual attached to the TaqMan Gene Expression. An mRNA amount of the specimen is calculated as a relative proportion when the mRNA amount of CKAP5 mRNA was defined as 1.

Figure 3:
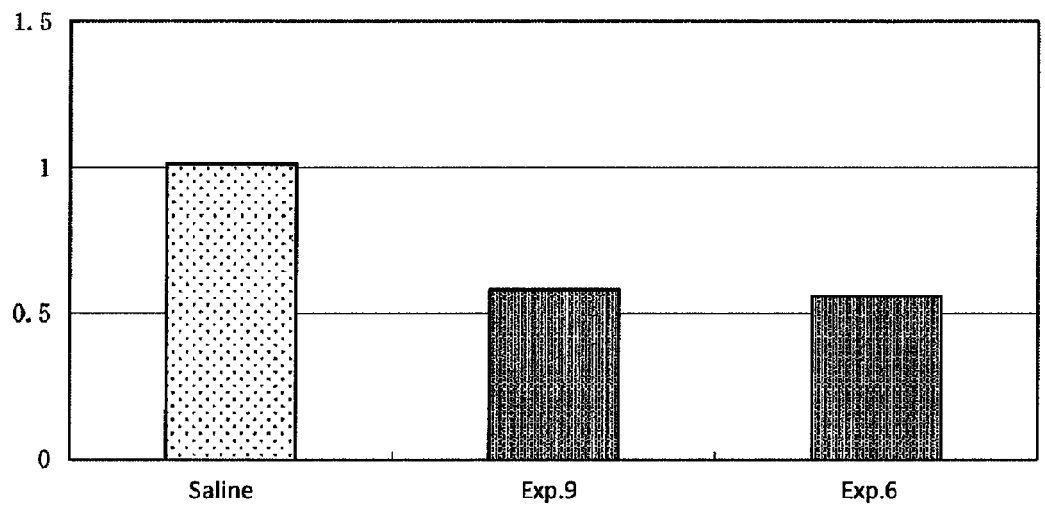
FIG. 3 shows an amount of CKAP5 mRNA in tumor 48 hours after the administration of the preparations obtained in Example 6 and Comparative Example 9 to MIA PaCa-2 xenograft mice in an amount equivalent to 10 mg/kg CKAP5 siRNA. The ordinate represents a relative value of an amount of CKAP5 mRNA while defining that of a saline-administered group as 1.

FIG. 3 shows an amount of CKAP5 mRNA in tumor 48 hours after the administration of the preparations obtained in Example 6 and 9 in an amount equivalent to 10 mg/kg siRNA. The ordinate represents a relative value of an amount of CKAP5 mRNA while defining that of a saline-administered group as 1.

Figure 4:
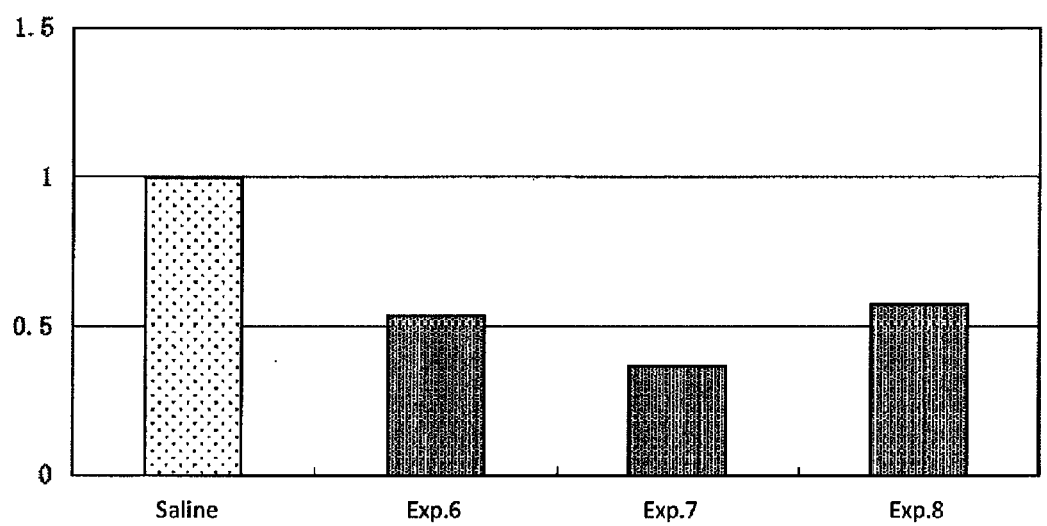
FIG. 4 shows an amount of CKAP5 mRNA in tumor 48 hours after the administration of the preparations obtained in Examples 6-8 to MIA PaCa-2 xenograft mice in an amount equivalent to 10 mg/kg CKAP5 siRNA. The ordinate represents a relative value of an amount of CKAP5 mRNA while defining that of a saline-administered group as 1. Meanings of ◇ and ■ on the graph are as the saline-administered group and the preparation obtained in Example 9-administered group.

FIG. 4 shows an amount of CKAP5 mRNA in tumor 48 hours after the administration of the preparations obtained in Examples 6 to 8 in an amount equivalent to 10 mg/kg siRNA. The ordinate represents a relative value of an amount of CKAP5 mRNA while defining that of a saline-administered group as 1.

TEST EXAMPLE 4

The preparation obtained in Example 9 (lipid nano particles containing Compound 1 and nucleic acid) was subjected to a tumor proliferation evaluation test in the following manner.

Similar to Test Example 3, the test was carried out using a xenograft model in which MIA PaCA-2 that is a cell line derived from pancreas cancer was transplanted in an SCID mouse. The mice were divided into groups consisting of six heads per group while taking the tumor volume as an index (Day 0), and the preparation obtained in Example 9 was intravenously administered to the mouse in a dose of 10 mg/kg (10 mL/kg) on Day 0 and Day 7, respectively. A saline was administered in a dose of 10 mL/kg. A tumor size of each individual was measured on from Day 0 to Day 14, and a tumor volume and a volume ratio were calculated according to the following equations.

Tumor volume ($mm^3$)=Major axis (mm)×Minor axis (mm)×Minor axis (mm)×0.5

Volume ratio (V/VO)=Tumor volume at each point of time ($mm^3$)÷Tumor volume on Day 0 ($mm^3$)

Figure 5:
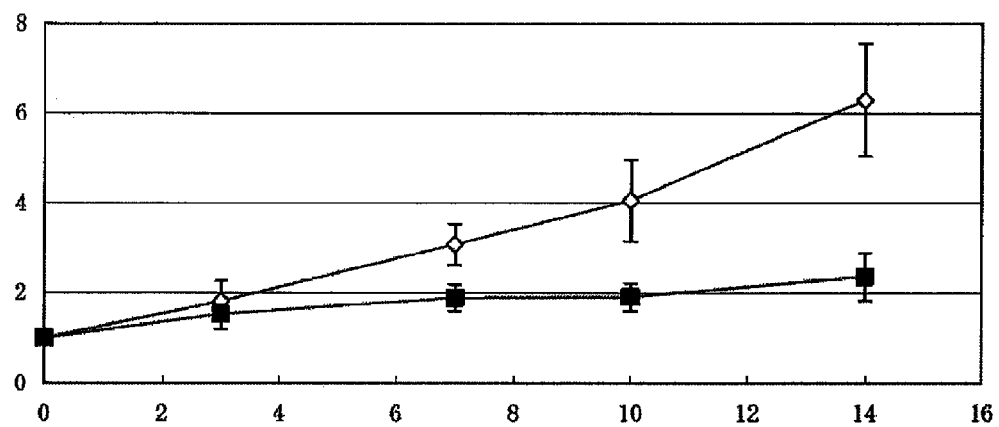
FIG. 5 shows a transition of a value of a tumor volume when the preparation obtained in Example 9 were administered on Day 0 and Day 7 to MIA PaCa-2 xenograft mice in an amount equivalent to 10 mg/kg CKAP5 siRNA. The ordinate represents a relative value of a tumor volume while defining that on Day 0 as 1. The abscissa represents a number of elapsed days after the start of experiment.

FIG. 5 shows a transition of a value of a tumor volume on Day 0 and Day 7 in a dose of 10 mg/kg (10 mL/kg). The ordinate represents a relative value of a tumor volume while defining that on Day 0 as 1. The abscissa represents a number of elapsed days after the start of experiment.

As is clear from FIGS. 3 to 5, the results of the in vivo efficacy evaluation test revealed that the preparations obtained in Examples 6 to 9 (lipid nano particles containing Compound (I) and CKAP5 siRNA suppresses expression of CKAP5 gene) had very strong suppression of expression of CKAP5 gene and have strong anti-tumor activity. The results of the in vivo efficacy evaluation test (Test Examples 3 and 4) revealed that the preparations in the present inventions had unexpectedly strong activity, although the preparations had weak transfection-activity in the results of the in vitro evaluation test (Test Example 1). It is found that the lipid nano particles are an outstanding lipid nanoparticle which carries out drug delivery satisfactorily into a cell in vivo. The effect is not expected by a person skilled in the art. Especially, it is found that the lipid nano particles are an outstanding lipid nanoparticle which carries out drug delivery satisfactorily into a tumor in vivo. The effect is not more expected by a person skilled in the art.

Therefore, it is found that the lipid nano particles of the present invention can be used to introduce nucleic acid into cell, and that Compound (I) is an outstanding cationic lipid which makes it easy to carry out drug delivery satisfactorily into a cell in vivo. In addition, it is found that the lipid nano particles of the present invention can be used to introduce nucleic acid into, especially, tumor cell, and that Compound (I) is an outstanding cationic lipid which makes it easy to carry out drug delivery satisfactorily into a tumor cell in vivo.

EXAMPLE 10

A preparation was produced in the following manner by using compound 1 obtained in Referential Example 1.

Commercially available Eg5 siRNA (Invitrogen; catalog No. HSS105842) was used as the nucleic acid. Eg5 siRNA suppresses expression of Eg5 gene and has a sense strand comprising base sequence 5'-CCCAUCAACACUG-GUAAGAACUGAA-3' (SEQ ID NO:5), and an antisense strand comprising base sequence 5'-UUCAGUUCUUAC-CAGUGUUGAUGGG-3' (SEQ ID NO:6). The annealed sense strand and the antisense strand was obtained from Invitrogen, and was used after being dissolved in distilled water so as to have a concentration of 24 mg/mL (hereinafter referred to as "Eg5 siRNA solution").

Compounds 1 and sodium 1,2-dimyristoyl-sn-glycero-3-phosphoethanolamine-N-(methoxy(polyethylene glycol)-2000) (PEG-DMPE Na, N-(carbonylmethoxypolyethylene glycol 2000)-1,2-dimyristoyl-sn-glycero-3-phosphoethanolamine sodium salt, manufactured by NOF Corporation) was suspended in a proportion of 57.3/5.52 mmol/L in an aqueous solution containing hydrochloric acid and ethanol, and stirring with a vortex mixer and heating was repeated, thereby obtaining a homogenous suspension. This suspension was allowed to pass through a 0.2-μm polycarbonate membrane filter and a 0.05-μm polycarbonate membrane filter at room temperature, thereby obtaining a dispersion liquid of lead particles. An average particle diameter of the lead particles obtained was measured by means of a dynamic light scattering (DLS) particle size analyzer and confirmed to fall within the range of from 30 nm to 100 nm. The Eg5 siRNA solution was mixed with the obtained dispersion liquid of lead particles in a proportion of 3/1, to which was then added distilled water in an amount of three times, and the contents were mixed to prepare a dispersion liquid of cationic lipid/nucleic acid complex particles.

On the other hand, each lipid was weighed in a proportion of compound 1 to sodium 1,2-distearoyl-sn-glycero-3-phosphoethanolamine-N-(methoxy(polyethylene glycol)-2000) (PEG-DSPE Na, N-(carbonylmethoxy polyethylene glycol 2000)-1,2-distearoyl-sn-glycro-3-phosphoethanolamine sodium salt, manufactured by NOF Corporation) to distearoyl phosphatidylcholine (DSPC, 1,2-distearoyl-sn-glycero-3-phosphocholine, manufactured by NOF Corporation) to cholesterol (manufactured by NOF Corporation) of 8.947/2.94/5.71/11.8 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/nucleic acid complex particle in proportion of 1/1. The mixture was further mixed with distilled water in an amount of several times, thereby obtaining a crude preparation.

The obtained crude preparation was concentrated using Amicon Ultra (manufactured by Millipore Corporation), further replaced with a saline, and then filtered with a 0.2-μm filter (manufactured by Toyo Roshi Kaisha, Ltd.) within a clean bench.

Furthermore, an siRNA concentration of the obtained preparation was measured, and the preparation was diluted with a saline such that the siRNA concentration was 1.0 mg/mL. An average particle diameter of lipid nano particles in the preparation was 80.3 nm.

EXAMPLE 11

A preparation was produced in the following manner by using Compound 1 obtained in Referential Example 1.

A dispersion liquid of cationic lipid/nucleic acid complex particles contained Eg5 siRNA and lead particles are obtained in the same manner as that in Example 10.

On the other hand, each lipid was weighed in a proportion of Compound 1 and Trans-1-methyl-3,4-bis(((9Z,12Z)-octadeca-9,12-dienoyloxy)methyl)pyrrolidine (The Compound was produced by a method described in WO2011/136368) to sodium 1,2-distearoyl-sn-glycero-3-phosphoethanolamine-N-(methoxy(polyethylene glycol)-2000) (PEG-DSPE Na, N-(carbonylmethoxy polyethylene glycol 2000)-1,2-distearoyl-sn-glycro-3-phosphoethanolamine sodium salt, manufactured by NOF Corporation) to distearoyl phosphatidylcholine (DSPC, 1,2-distearoyl-sn-glycero-3-phosphocholine, manufactured by NOF Corporation) to cholesterol (manufactured by NOF Corporation) of 2.982/5.965/2.943/5.707/11.83 mmol/L and dissolved in 90 vol % ethanol, thereby preparing a solution of lipid membrane constituent components.

The obtained solution of lipid membrane constituent components was heated and then mixed with the obtained dispersion liquid of cationic lipid/nucleic acid complex particle in a proportion of 1/1. The mixture was further mixed with distilled water in an amount of several times, thereby obtaining a crude preparation.

The obtained crude preparation was concentrated using Amicon Ultra (manufactured by Millipore Corporation), further replaced with a saline, and then filtered with a 0.2-μm filter (manufactured by Toyo Roshi Kaisha, Ltd.) within a clean bench. Furthermore, an siRNA concentration of the obtained preparation was measured, and the preparation was diluted with a saline such that the siRNA concentration was 1.0 mg/mL. An average particle diameter of lipid nano particles in the preparation was 80.5 nm.

TEST EXAMPLE 5

The preparations obtained in Examples 10 and 11 (lipid nano particles comprising Compound 1 and nucleic acid) were subjected to an in vivo mRNA knockdown evaluation test in the following manner.

Similar to Test Example 3, the test was carried out using a xenograft model in which MIA PaCA-2 that is a cell line derived from pancreas cancer was transplanted in an SCID mouse. Six days after the transplantation, the mice were divided into groups consisting of three heads per group while taking the tumor volume as an index, and each of the preparations in Examples 10 and 11 is intravenously administered in a dose of 10 mg/kg (10 mL/kg). As a saline-administered group, a saline was administered in a dose of 10 mL/kg. Before the administration and 48 hours after the administration, the weight of the mouse was measured. After the weight measurement, the mouse is euthanized, and the subcutaneous tumor is removed. The removed tumor was immediately frozen by liquid nitrogen and stored at −80° C. until it is used.

With respect to the obtained tumor sample, 1 mL of a Trizol reagent (manufactured by Invitrogen, 15596-018) and zirconia beads of 5 mm were added to a 2-mL round bottom tube containing the sample charged therein, and the contents were pulverized by Tissue lyser II (manufactured by QIAGEN) under conditions of 1/25 freq, 1.5 minutes×2 times. After the pulverization, centrifugation (at 10,000 rpm for 10 minutes) were conducted, the supernatant was recovered, to which was then added 200 μL of chloroform, and the contents were vigorously stirred, followed by again conducting centrifugation (at 15,000 rpm for 15 min). 200 μL of the obtained supernatant was extracted RNA using a automated nucleic acid extractor MagNA PURE (Roche) and Cellular RNA Large Volume Kit (Roche, 5467535). A concentration of the extracted RNA was measured by a trace absorption photometer Dropsense96 (Trinean), and RNA corresponding to from 200 to 1,000 ng was subjected to reverse transfer with a Transcriptor (manufactured by Roche, 4897030). The reaction solution and the reaction condition followed those described in the appended papers. The obtained cDNA sample is diluted ten times with dH$_2$0 and used as a template of qPCR. For the qPCR reaction, TaqMan Gene Expression Master Mix (manufactured by Applied Biosystems, 4369542) and TaqMan Gene Expression Assays (manufactured by Applied Biosystems, 4331182) were used. The conditions of the PCR reaction follows those described in the instruction manual attached to the TaqMan Gene Expression. An mRNA amount of the specimen is calculated as a relative proportion when the mRNA amount of Eg5 mRNA was defined as 1.

Figure 6:
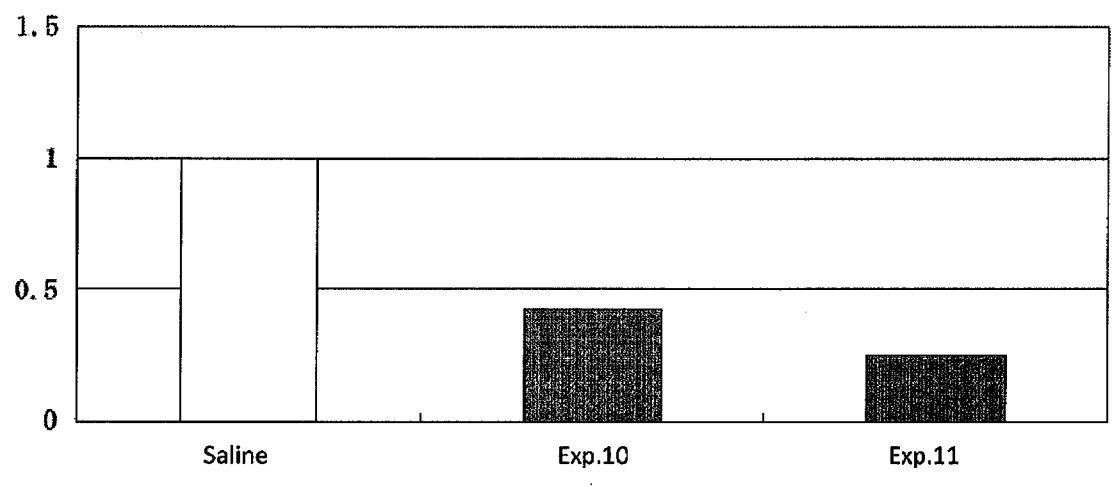
FIG. 6 shows an amount of Eg5 mRNA in tumor 48 hours after the administration of the preparations obtained in Example 10 and 11 to MIAPaCa-2 xenograft mice in an amount equivalent to 10 mg/kg Eg5 siRNA. The ordinate represents a relative value of an amount of Eg5 mRNA while defining that of a saline-administered group as 1.

FIG. 6 shows an amount of Eg5 mRNA in tumor 48 hours after the administration of the preparations obtained in Examples 10 and in an amount equivalent to 10 mg/kg siRNA. The ordinate represents a relative value of an amount of Eg5 mRNA while defining that of a saline-administered group as 1.

TEST EXAMPLE 6

The preparation obtained in Example 11 (lipid nano particles containing Compound 1 and nucleic acid) was subjected to a tumor proliferation inhibition-evaluation test in the following manner.

Similar to Test Example 1, the test was carried out using a xenograft model in which MIA PaCA-2 that is a cell line derived from pancreas cancer was transplanted in an SCID mouse. The mice were divided into groups consisting of six heads per group while taking the tumor volume as an index (Day 0), and the preparation obtained in Example 9 was intravenously administered to the mouse in a dose of 10 mg/kg (10 mL/kg). A saline was administered in a dose of 10 mL/kg. The tumor size of each individual was measured on Day 0 to Day 5, and the tumor volume and the volume ratio were calculated according to the methods used in Test Example 4.

Figure 7:
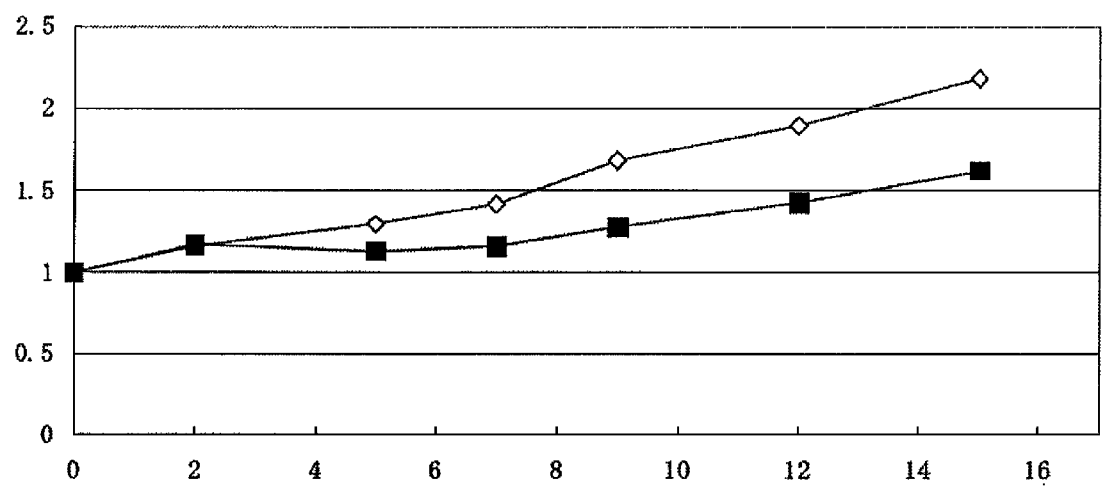
FIG. 7 shows a transition of a value of a tumor volume when the preparation obtained in Example 11 were administered on Day 0 to MIA PaCa-2 xenograft mice in an amount equivalent to 10 mg/kg Eg5 siRNA. The ordinate represents a relative value of a tumor volume while defining that on Day 0 as 1. The abscissa represents a number of elapsed days after the start of experiment. Meanings of ◇ and ■ on the graph are as the saline-administered group and the preparation obtained in Example 11-administered group.

FIG. 7 shows a transition of a value of a tumor volume on Day 0 in a dose of 10 mg/kg (10 mL/kg). The ordinate represents a relative value of a tumor volume while defining that on Day 0 as 1. The abscissa represents a number of elapsed days after the start of experiment.

As is clear from FIGS. 6 and 7, the results of the in vivo efficacy evaluation test revealed that the preparations obtained in Examples 10 and 11 (lipid nano particles containing Compound 1 and Eg5 siRNA suppresses expression of Eg5 gene) had very strong suppression of expression of Eg5 gene and have strong anti-tumor activity. The results of the in vivo efficacy evaluation test (Test Examples 5 and 6) revealed that the preparations in the present inventions had unexpectedly strong activity, although the preparations had weak transfection-activity in the results of the in vitro evaluation test (Test Example 1). It is found that the lipid nano particles are an outstanding lipid nanoparticle which carries out drug delivery satisfactorily into a cell in vivo. The effect is not expected by a person skilled in the art. Especially, it is found that the lipid nano particles are an outstanding lipid nanoparticle which carries out drug delivery satisfactorily into a tumor in vivo. The effect is not more expected by a person skilled in the art.

Therefore, it is found that the lipid nano particles of the present invention can be used to introduce nucleic acid into cell, and that Compound (I) is an outstanding cationic lipid which makes it easy to carry out drug delivery satisfactorily into a cell in vivo. In addition, it is found that the lipid nano particles of the present invention can be used to introduce nucleic acid into, especially, tumor cell, and that Compound (I) is an outstanding cationic lipid which makes it easy to carry out drug delivery satisfactorily into a tumor cell in vivo.

INDUSTRIAL APPLICABILITY

The lipid nano particles of the present invention can be administered to mammals, etc and, for example, the like to easily introduce the nucleic acid into cells and the like.

SEQUENCE LISTING FREE TEXT

SEQ No. 1: siRNA sense
SEQ No. 2: siRNA antisense
SEQ No. 2: 5'-phosphorylated Adenosine
SEQ No. 3: siRNA sense
SEQ No. 4: siRNA antisense
SEQ No. 4: 5'-phosphorylated Adenosine
SEQ No. 5: siRNA sense
SEQ No. 6: siRNA antisense
[Sequence Listing]
SEQUENCE LISTING1001P12211.txt

---

The invention claimed is:

1. Lipid nano particles for drug delivery comprising; a cationic lipid of formula (l):

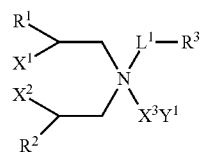

wherein:
R$^1$ and R$^2$ are, the same or different, each linear or branched alkyl, alkenyl or alkynyl having 10 to 24 carbon atoms,
X$^1$ and X$^2$ are hydrogen atoms, or are combined together to form a single bond or alkylene,
X$^3$ and Y$^1$ are absent,
L$^1$ is , —CO— or —CO—O—, R$^3$ is pyrrolidin-2-yl, pyrrolidin-3-yl, piperidin-2-yl, piperidin-3-yl, piperidin-4-yl, morpholin-2-yl, morpholin-3-yl, or alkyl having 1 to 6 carbon atoms or alkenyl having 3 to 6 carbon atoms substituted with 1 to 3 substituent(s), which is(are), the same or different, hydroxy, alkoxy, carbamoyl, monoalkylcarbamoyl, dialkylcarbamoyl, pyrrolidinyl, piperidyl or morpholinyl.

2. The lipid nano particles for drug delivery according to claim 1, wherein R$^1$ and R$^2$ are dodecyl, tetradecyl, (Z)-dodec-7-enyl, (Z)-tetradec-7-enyl, (Z)-hexadec-4-enyl, (Z)-hex adec-7-enyl, (E)-hexadec-7-enyl, (Z)-hexadec-9-enyl, (7Z,10Z)-hexadec-7,10-dienyl, (7Z,10Z,13Z)-hexadec-7,10,13-trienyl, (Z)-octadec-9-enyl or (9Z,12Z)-octadec-9,12-dienyl.

3. The lipid nano particles for drug delivery according to claim 1, wherein R$^1$ and R$^2$ are tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl or (11Z,14Z)-icosa-11,14-dienyl.

4. The lipid nano particles for drug delivery according to claim 1, wherein L$^1$ is —CO— or —CO—O—, R$^3$ is pyrrolidin-3-yl, piperidin-3-yl, piperidin-4-yl, or alkyl having 1 to 6 carbon atoms or alkenyl having 3 to 6 carbon atoms substituted with 1 to 3 substituent(s), which is(are), the same or different, hydroxy, alkoxy, carbamoyl, monoalkylcarbamoyl, dialkylcarbamoyl, pyrrolidinyl, piperidyl or morpholinyl.

5. The lipid nano particles for drug delivery according to claim 1, wherein X$^1$ and X$^2$ are combined together to form a single bond or alkylene.

6. The lipid nano particles for drug delivery according to claim 1, wherein X$^1$ and X$^2$ are combined together to form a single bond or alkylene, and
R$^3$ is methyl or alkyl having a carbon number of from 1 to 6 or alkenyl having a carbon number of from 3 to 6, each substituted with 1 to 3 substituent(s), which is(are), the same or different, hydroxy or carbamoyl.

7. The lipid nano particles for drug delivery according to claim 1, wherein X$^1$ and X$^2$ are hydrogen atoms, and
R$^3$ is methyl or alkyl having a carbon number of from 1 to 6 or alkenyl having a carbon number of from 3 to 6, each substituted with 1 to 3 substituent(s), which is(are), the same or different, hydroxy or carbamoyl.

8. The lipid nano particles for drug delivery according to claim 1, which comprise a nucleic acid as drug.

9. The lipid nano particles for drug delivery according to claim 8, wherein the cationic lipid forms a complex together with the nucleic acid, or forms a complex between a combination of the cationic lipid with a neutral lipid and/or a polymer and the nucleic acid.

10. The lipid nano particles for drug delivery according to claim 8, wherein the cationic lipid forms a complex together with the nucleic acid, or forms a complex between a combination of the cationic lipid with a neutral lipid and/or a polymer and the nucleic acid, and the composition comprises the complex and a lipid membrane for encapsulating the complex.

11. The lipid nano particles for drug delivery according to claim 8, wherein the nucleic acid is a nucleic acid having an activity of suppressing the expression of the target gene by utilizing RNA interference (RNAi).

12. The lipid nano particles for drug delivery according to claim 11, wherein the target gene is a gene associated with tumor or inflammation.

13. A method for introducing the nucleic acid into a cell by using the lipid nano particles for drug delivery of claim 8.

14. The method according to claim 13, wherein the cell is a cell at a tumor or inflammation site of a mammal.

15. The method according to claim 13, wherein the cell is a cell in the liver, lungs, kidneys or spleen of a mammal.

16. The method according to claim 14, wherein the method of the introduction into a cell is a method of introduction into a cell by intravenous administration.

17. A method for treating cancer or inflammatory disease, the method including administering the lipid nano particles for drug delivery of claim 1 to a mammal.

18. The method according to claim 17, wherein the method of administration is intravenous administration.

\* \* \* \* \*

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<223> OTHER INFORMATION: siRNA sense
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
```

```
<222> LOCATION: (15)..(15)
<223> OTHER INFORMATION: um
<220> FEATURE:
<221> NAME/KEY: modified_base
<222> LOCATION: (21)..(21)
<223> OTHER INFORMATION: um

<400> SEQUENCE: 1
gucaucacac ugaauaccaa u                                              21

<210> SEQ ID NO 2
<211> LENGTH: 23
<212> TYPE: RNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (1)..(1)
<223> OTHER INFORMATION: 5'-phosphorylated Adenosine

<400> SEQUENCE: 2
auugguauuc agugugauga cac                                            23

<210> SEQ ID NO 3
<211> LENGTH: 25
<212> TYPE: RNA
<213> ORGANISM: Artificial Sequence
<220> FEATURE:
<223> OTHER INFORMATION: siRNA sense
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (24)..(24)
<223> OTHER INFORMATION: um
<220> FEATURE:
<221> NAME/KEY: modified_base
<222> LOCATION: (25)..(25)
<223> OTHER INFORMATION: am

<400> SEQUENCE: 3
ggaagcuggc gauuaugcag auuua                                          25

<210> SEQ ID NO 4
<211> LENGTH: 25
<212> TYPE: RNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (1)..(1)
<223> OTHER INFORMATION: 5'-phosphorylated Adenosine

<400> SEQUENCE: 4
uaaaucugca uaaucgccag cuucc                                          25

<210> SEQ ID NO 5
<211> LENGTH: 25
<212> TYPE: RNA
<213> ORGANISM: Artificial Sequence
<220> FEATURE:
<223> OTHER INFORMATION: siRNA sense
```

```
<400> SEQUENCE: 5
cccaucaaca cugguaagaa cugaa                                                25

<210> SEQ ID NO 6
<211> LENGTH: 25
<212> TYPE: RNA
<213> ORGANISM: Artificial Sequence
<220> FEATURE:
<223> OTHER INFORMATION: siRNA antisense

<400> SEQUENCE: 6
uucaguucuu accaguguug auggg                                                25
```